(12) United States Patent
Viola

(10) Patent No.: US 7,740,160 B2
(45) Date of Patent: *Jun. 22, 2010

(54) SURGICAL STAPLING APPARATUS HAVING A WOUND CLOSURE MATERIAL APPLICATOR ASSEMBLY

(75) Inventor: Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/642,215

(22) Filed: Dec. 20, 2006

(65) Prior Publication Data

US 2007/0125827 A1    Jun. 7, 2007

Related U.S. Application Data

(63) Continuation of application No. 10/513,421, filed as application No. PCT/US03/014699 on May 9, 2003, now Pat. No. 7,238,195.

(60) Provisional application No. 60/379,971, filed on May 10, 2002.

(51) Int. Cl.
    *A61D 1/00* (2006.01)
(52) U.S. Cl. ............................ 227/180.1; 606/213
(58) Field of Classification Search .......... 606/214, 606/219, 220; 227/175.1–182.1, 19
    See application file for complete search history.

(56) References Cited

U.S. PATENT DOCUMENTS

| | | | |
|---|---|---|---|
| 960,300 | A | 6/1910 | Fischer |
| 2,301,622 | A | 11/1942 | Hambrecht |
| 2,853,074 | A | 9/1958 | Olson |
| 2,874,384 | A | 2/1959 | Krone |
| 2,891,250 | A | 6/1959 | Hirata |
| 3,079,606 | A | 3/1963 | Bobrov et al. |
| 3,080,564 | A | 3/1963 | Strekopov et al. |
| 3,252,643 | A | 5/1966 | Strekopov et al. |
| 3,269,630 | A | 8/1966 | Fleischer |
| 3,275,211 | A | 9/1966 | Hirsch et al. |

(Continued)

FOREIGN PATENT DOCUMENTS

EP    0514185 A1    11/1992

(Continued)

OTHER PUBLICATIONS

Office Action cited in U.S. Appl. No. 10/513,421 dated Jun. 1, 2006 (20 pages).

(Continued)

*Primary Examiner*—Todd E Manahan
*Assistant Examiner*—Eric Blatt

(57) ABSTRACT

A surgical stapling apparatus includes a staple anvil and a staple cartridge having a working surface, one or more rows of individual staple slots formed in the working surface, a knife track formed along a length of the working surface, and a plurality of surgical staples individually disposed within the individual staple slots. The apparatus further includes an actuation sled having a knife and being configured and adapted to movably position the knife axially within the knife track. The apparatus also includes a wound closure material applicator assembly having a needle secured to the knife to dispense a quantity of wound closure material along a length of the knife track as the actuation sled and knife are moved therealong.

21 Claims, 20 Drawing Sheets

U.S. PATENT DOCUMENTS

| | | |
|---|---|---|
| 3,278,107 A | 10/1966 | Rygg |
| 3,315,863 A | 4/1967 | O'Dea |
| 3,490,675 A | 1/1970 | Green et al. |
| 3,499,591 A | 3/1970 | Green |
| 3,589,589 A | 6/1971 | Akopov et al. |
| 3,598,299 A | 8/1971 | Johnson |
| 3,692,224 A | 9/1972 | Astafiev et al. |
| 3,795,034 A | 3/1974 | Strekopov et al. |
| 3,889,683 A | 6/1975 | Kapotanov et al. |
| 3,935,981 A | 2/1976 | Akopov et al. |
| 3,949,923 A | 4/1976 | Akopov et al. |
| 3,973,709 A | 8/1976 | Akopov et al. |
| 4,047,654 A | 9/1977 | Alvarado |
| 4,111,206 A | 9/1978 | Vishnevsky et al. |
| 4,162,678 A | 7/1979 | Fedetov et al. |
| 4,216,890 A | 8/1980 | Akopov et al. |
| 4,216,891 A | 8/1980 | Behlke |
| 4,272,002 A | 6/1981 | Moshofsky |
| 4,290,542 A | 9/1981 | Fedetov et al. |
| 4,296,881 A | 10/1981 | Lee |
| 4,316,468 A | 2/1982 | Klieman et al. |
| 4,317,105 A | 2/1982 | Sinha et al. |
| 4,325,376 A | 4/1982 | Klieman et al. |
| 4,378,901 A | 4/1983 | Akopov et al. |
| 4,392,493 A | 7/1983 | Niemeijer |
| 4,397,311 A | 8/1983 | Kanshin et al. |
| 4,429,695 A | 2/1984 | Green et al. |
| 4,442,964 A | 4/1984 | Becht |
| 4,453,661 A | 6/1984 | Genyk et al. |
| 4,470,533 A | 9/1984 | Schuler |
| 4,477,007 A | 10/1984 | Foslien |
| 4,485,811 A | 12/1984 | Chemousov et al. |
| 4,527,724 A | 7/1985 | Chow et al. |
| 4,550,870 A | 11/1985 | Krumme et al. |
| 4,570,633 A | 2/1986 | Golden |
| 4,585,153 A | 4/1986 | Failla et al. |
| 4,596,351 A | 6/1986 | Fedetov et al. |
| 4,605,001 A | 8/1986 | Rothfuss et al. |
| 4,607,636 A | 8/1986 | Kula et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,648,542 A | 3/1987 | Fox et al. |
| 4,684,051 A | 8/1987 | Akopov et al. |
| 4,741,336 A | 5/1988 | Failla et al. |
| 4,784,137 A | 11/1988 | Kulik et al. |
| 4,805,823 A | 2/1989 | Rothfuss |
| 4,848,637 A | 7/1989 | Pruitt |
| 4,863,088 A | 9/1989 | Redmond et al. |
| 4,892,244 A | 1/1990 | Fox et al. |
| 4,930,503 A | 6/1990 | Pruitt |
| 4,991,764 A | 2/1991 | Mericle |
| 5,005,754 A | 4/1991 | Vam Overloop |
| 5,018,657 A | 5/1991 | Pedlick et al. |
| 5,065,929 A | 11/1991 | Schulze et al. |
| 5,074,454 A | 12/1991 | Peters |
| 5,083,695 A | 1/1992 | Foslien et al. |
| 5,111,987 A | 5/1992 | Moeinzadeh et al. |
| 5,129,570 A | 7/1992 | Schulze et al. |
| 5,137,198 A | 8/1992 | Nobis et al. |
| 5,141,144 A | 8/1992 | Foslien et al. |
| 5,156,613 A | 10/1992 | Sawyer |
| 5,156,614 A | 10/1992 | Green et al. |
| 5,170,925 A | 12/1992 | Madden et al. |
| 5,172,845 A | 12/1992 | Tejeiro |
| 5,180,092 A | 1/1993 | Crainich |
| 5,188,274 A | 2/1993 | Moeinzadeh et al. |
| 5,205,459 A | 4/1993 | Brinkerhoff et al. |
| 5,240,163 A | 8/1993 | Stein et al. |
| 5,254,113 A | 10/1993 | Wilk |
| 5,263,629 A | 11/1993 | Trumbill et al. |
| RE34,519 E | 1/1994 | Fox et al. |
| 5,275,322 A | 1/1994 | Brinkerhoff et al. |
| 5,292,053 A | 3/1994 | Bilotti et al. |
| 5,307,976 A | 5/1994 | Olson et al. |
| 5,312,024 A | 5/1994 | Grant et al. |
| 5,332,142 A | 7/1994 | Robinson et al. |
| 5,344,061 A | 9/1994 | Crainich |
| 5,364,003 A | 11/1994 | Williamson, IV |
| 5,376,095 A | 12/1994 | Ortiz |
| 5,381,943 A | 1/1995 | Allen et al. |
| 5,383,880 A | 1/1995 | Hooven |
| 5,395,033 A | 3/1995 | Byrne et al. |
| 5,395,034 A | 3/1995 | Allen et al. |
| 5,397,324 A | 3/1995 | Carroll et al. |
| 5,405,073 A | 4/1995 | Porter |
| 5,415,334 A | 5/1995 | Williamson, IV et al. |
| 5,415,335 A | 5/1995 | Knodell, Jr. |
| 5,417,361 A | 5/1995 | Williamson, IV |
| 5,431,323 A | 7/1995 | Smith et al. |
| 5,433,721 A | 7/1995 | Hooven et al. |
| 5,439,156 A | 8/1995 | Grant et al. |
| 5,445,304 A | 8/1995 | Plyley et al. |
| 5,447,265 A | 9/1995 | Vidal et al. |
| 5,452,836 A | 9/1995 | Huiteman et al. |
| 5,452,837 A | 9/1995 | Williamson, IV et al. |
| 5,458,279 A | 10/1995 | Plyley |
| 5,465,894 A | 11/1995 | Clark et al. |
| 5,465,895 A | 11/1995 | Knodel et al. |
| 5,470,007 A | 11/1995 | Plyley et al. |
| 5,470,010 A | 11/1995 | Rothfuss et al. |
| 5,484,451 A | 1/1996 | Akopov et al. |
| 5,485,947 A | 1/1996 | Olson et al. |
| 5,487,500 A | 1/1996 | Knodel et al. |
| 5,489,058 A | 2/1996 | Plyley et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,937 A | 7/1996 | Boiarski et al. |
| 5,547,117 A | 8/1996 | Hamblin et al. |
| 5,549,628 A | 8/1996 | Cooper et al. |
| 5,551,622 A | 9/1996 | Yoon |
| 5,553,765 A | 9/1996 | Knodel et al. |
| 5,562,239 A | 10/1996 | Boiarski et al. |
| 5,562,241 A | 10/1996 | Knodel et al. |
| 5,564,615 A | 10/1996 | Bishop et al. |
| 5,575,803 A | 11/1996 | Cooper et al. |
| 5,580,067 A | 12/1996 | Hamblin et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,609,285 A | 3/1997 | Grant et al. |
| 5,620,073 A * | 4/1997 | Marks ..................... 192/43.2 |
| 5,624,452 A | 4/1997 | Yates |
| 5,630,541 A | 5/1997 | Williamson, IV et al. |
| 5,632,432 A | 5/1997 | Schulze et al. |
| 5,632,433 A | 5/1997 | Grant et al. |
| 5,634,584 A | 6/1997 | Okorocha et al. |
| 5,641,111 A | 6/1997 | Ahrens et al. |
| 5,655,698 A | 8/1997 | Yoon |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,665,085 A | 9/1997 | Nardella et al. |
| 5,667,517 A | 9/1997 | Hooven |
| 5,669,544 A | 9/1997 | Schulze et al. |

| Patent | Date | Inventor |
|---|---|---|
| 5,669,934 A | 9/1997 | Sawyer |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley et al. |
| 5,680,982 A | 10/1997 | Schulze et al. |
| 5,690,675 A | 11/1997 | Sawyer et al. |
| 5,692,668 A | 12/1997 | Schulze et al. |
| 5,697,542 A | 12/1997 | Knodel et al. |
| 5,697,543 A | 12/1997 | Burdorff |
| 5,702,409 A | 12/1997 | Rayburn et al. |
| 5,704,534 A | 1/1998 | Huitema et al. |
| 5,716,366 A | 2/1998 | Yates |
| 5,725,554 A | 3/1998 | Simon et al. |
| 5,732,871 A | 3/1998 | Clark et al. |
| 5,735,848 A | 4/1998 | Yates et al. |
| 5,749,893 A | 5/1998 | Vidal et al. |
| 5,749,895 A | 5/1998 | Sawyer et al. |
| 5,752,965 A | 5/1998 | Francis et al. |
| 5,762,255 A | 6/1998 | Chrisman et al. |
| 5,769,303 A | 6/1998 | Knodel et al. |
| 5,769,892 A | 6/1998 | Kingwell |
| 5,779,132 A | 7/1998 | Knodel et al. |
| 5,785,232 A | 7/1998 | Vidal et al. |
| 5,794,834 A | 8/1998 | Hamblin et al. |
| 5,797,537 A | 8/1998 | Oberlin et al. |
| 5,810,240 A | 9/1998 | Robertson |
| 5,810,811 A | 9/1998 | Yates et al. |
| 5,810,855 A | 9/1998 | Rayburn et al. |
| 5,820,009 A | 10/1998 | Melling et al. |
| 5,824,015 A | 10/1998 | Sawyer |
| 5,826,776 A | 10/1998 | Schulze et al. |
| 5,855,311 A | 1/1999 | Hamblin et al. |
| 5,871,135 A | 2/1999 | Williamson, IV et al. |
| 5,878,938 A | 3/1999 | Bittner et al. |
| 5,895,412 A | 4/1999 | Tucker |
| 5,919,198 A | 7/1999 | Graves, Jr. et al. |
| 5,954,259 A | 9/1999 | Viola et al. |
| 5,988,479 A | 11/1999 | Palmer |
| 5,989,215 A | 11/1999 | Delmotte et al. |
| 6,010,054 A | 1/2000 | Johnson et al. |
| 6,045,560 A | 4/2000 | McKean et al. |
| 6,099,551 A | 8/2000 | Gabbay |
| 6,131,789 A | 10/2000 | Schulze et al. |
| 6,131,790 A | 10/2000 | Piraka |
| 6,264,087 B1 | 7/2001 | Whitman |
| 6,287,323 B1 | 9/2001 | Hammerslag |
| 6,315,183 B1 | 11/2001 | Piraka |
| 6,325,810 B1 | 12/2001 | Hamilton et al. |
| 6,398,797 B2 | 6/2002 | Bombard et al. |
| 6,451,029 B1 | 9/2002 | Yeatman |
| 6,488,197 B1 * | 12/2002 | Whitman .................. 227/180.1 |
| 6,491,201 B1 | 12/2002 | Whitman |
| 6,681,979 B2 | 1/2004 | Whitman |
| 6,695,199 B2 | 2/2004 | Whitman |
| 7,238,195 B2 * | 7/2007 | Viola .......................... 606/219 |
| 2002/0026159 A1 | 2/2002 | Zhu et al. |
| 2002/0049454 A1 | 4/2002 | Whitman et al. |
| 2003/0073981 A1 | 4/2003 | Whitman et al. |
| 2003/0089757 A1 | 5/2003 | Whitman |
| 2004/0092960 A1 | 5/2004 | Abrams et al. |
| 2007/0075116 A1 * | 4/2007 | Whitman .................. 227/176.1 |

FOREIGN PATENT DOCUMENTS

| | | |
|---|---|---|
| EP | 0625335 A1 | 11/1994 |
| EP | 0639349 A2 | 2/1995 |
| WO | WO02/30297 A2 | 4/2002 |

OTHER PUBLICATIONS

Office Action cited in U.S. Appl. No. 10/513,421 dated Oct. 30, 2006 (9 pages).
Office Action cited in U.S. Appl. No. 10/513,421 dated Jan. 22, 2007 (3 pages).
Office Action cited in U.S. Appl. No. 11/726,681 dated Sep. 18, 2007 (19 pages).
International Search Report from Application No. PCT/US05/37265 dated Apr. 24, 2008.

* cited by examiner

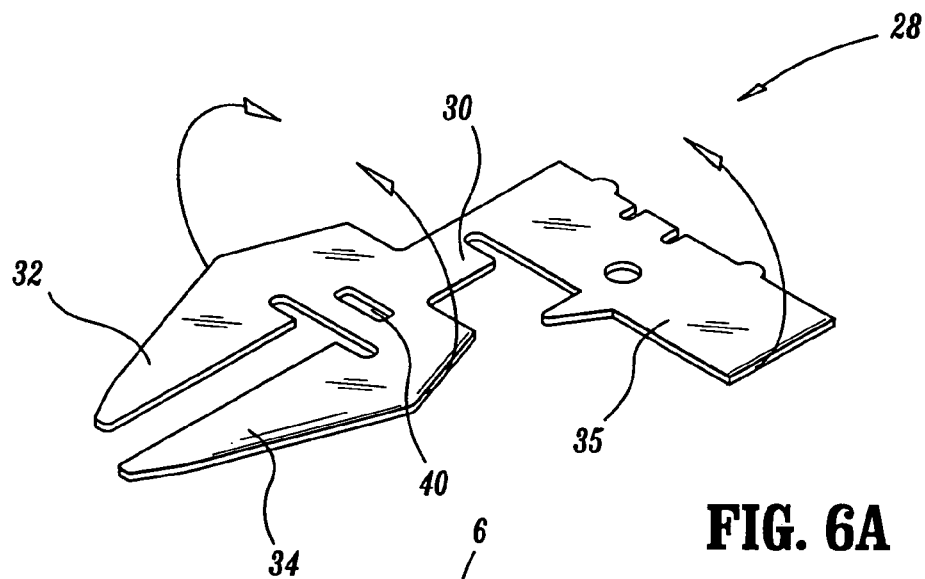
FIG. 6A
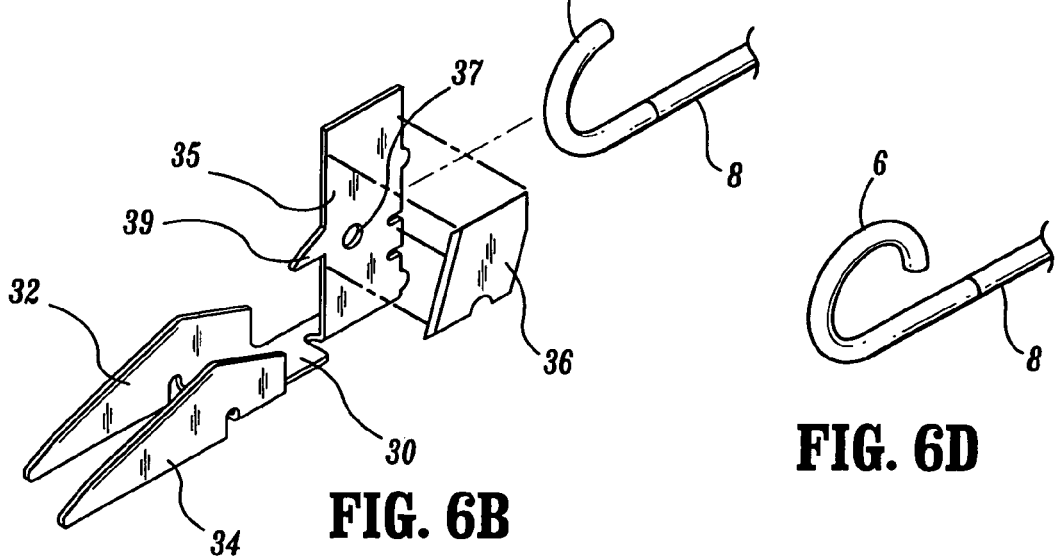
FIG. 6B
FIG. 6D
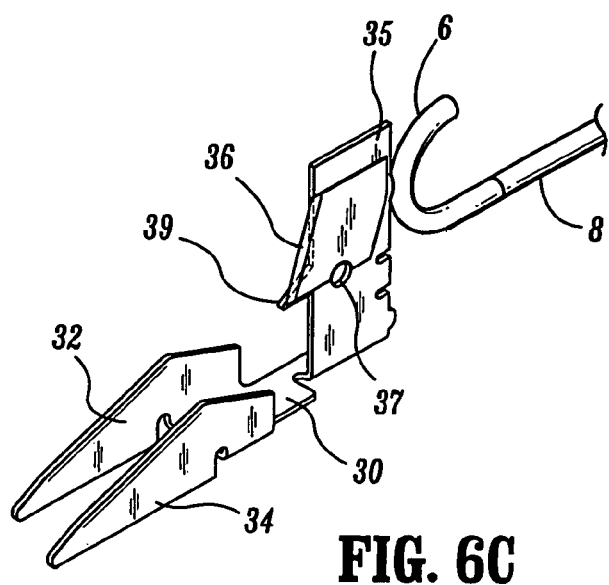
FIG. 6C

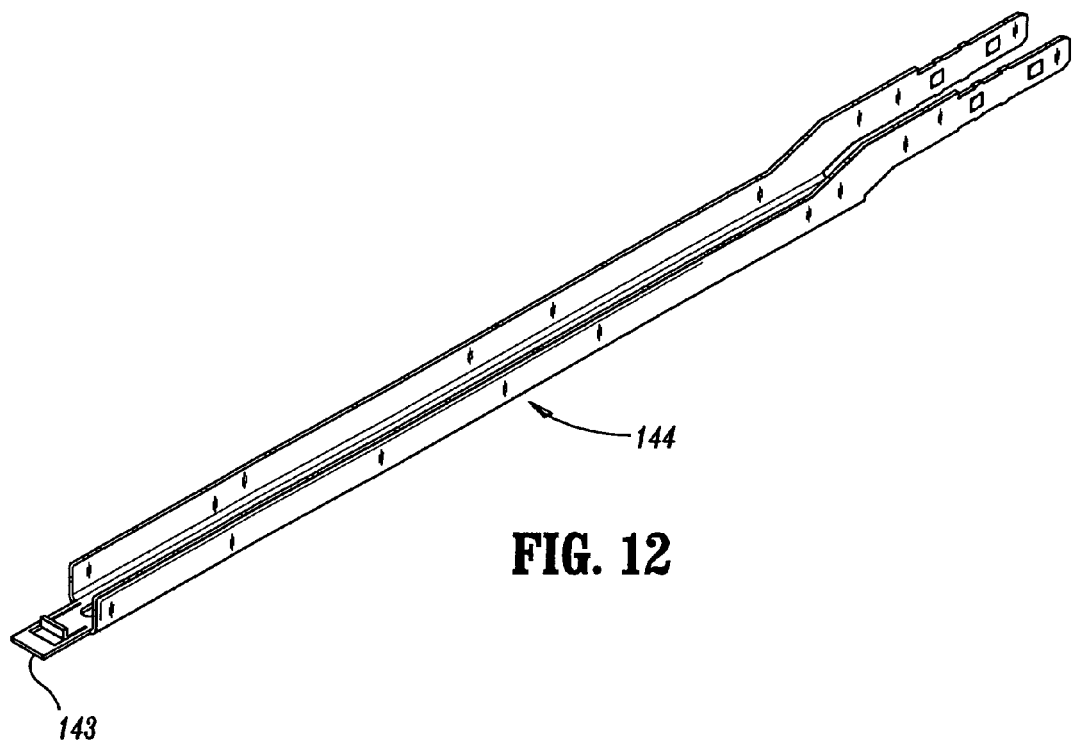
FIG. 12
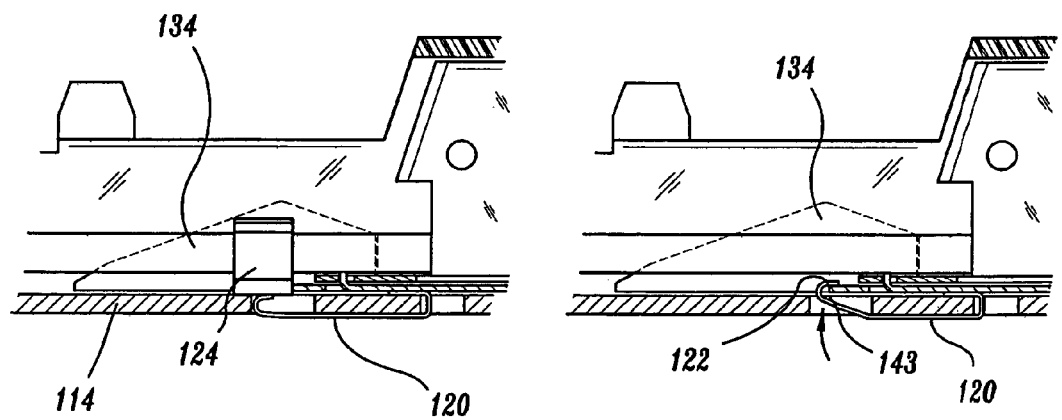
FIG. 13A     FIG. 13B

SURGICAL STAPLING APPARATUS HAVING A WOUND CLOSURE MATERIAL APPLICATOR ASSEMBLY

RELATED APPLICATIONS

This application is a continuation of U.S. patent application Ser. No. 10/513,421 filed Nov. 2, 2004 now U.S. Pat. No. 7,238,195 which is a National Stage Application of PCT/US03/14699 under 35 USC 371 (a), which claims priority of U.S. Provisional Patent Application Ser. No. 60/379,971 filed May 10, 2002, the entire contents of which are hereby incorporated by reference.

BACKGROUND

1. Technical Field

The present disclosure relates to surgical staplers, and more particularly, to a surgical stapling apparatus for applying a plurality of surgical fasteners to body tissue and having a wound closure material applicator assembly for dispensing a quantity of wound closure material or components thereof, at least along a knife cut line and/or a staple line.

2. Background of Related Art

Surgical procedures requiring cutting of tissue can result in bleeding at the site of the cut. Various techniques have been developed to control bleeding with varying degrees of success, such as, for example, suturing, applying clips to blood vessels, and using surgical fasteners, as well as electrocautery and other tissue healing techniques.

Surgical instruments using surgical fasteners entail grasping or clamping tissue between opposing Jaw structure and then joining the tissue by employing the surgical fasteners. These instruments are well known in the art. In some instruments, a knife is provided to cut the tissue, which has been joined by the fasteners. The fasteners are typically in the form of surgical staples however, two part polymeric fasteners can also be utilized.

Instruments for this purpose can include two elongated or circular members, which are respectively used to capture or clamp tissue. Typically, one of the members carries a cartridge, which houses a plurality of staples arranged in at least two lateral rows while the other member carries an anvil, which defines a surface for forming the staple legs as the staples are driven from the cartridge. Where two part fasteners are used, one of the members carries a cartridge which houses one half of a fastener while the other member carries the second part of the fastener, e.g., the mating part, which halves are configured and adapted to be held together upon approximation. Typically, the stapling operation is effected by a driving member, which travels longitudinally through the cartridge carrying member, with the driving member acting upon pushers, which engage the staples for sequentially ejecting them from the cartridge. A knife can be provided which travels between the staple rows to longitudinally cut (i.e., form a knife cut line) and/or open the stapled tissue between the rows of staples. Usually, but not always, the knife is associated with or travels with the staple driving member. Such instruments are disclosed in U.S. Pat. Nos. 3,079,606 and 3,490,675, the entire contents of which are incorporated herein by reference.

A later stapler disclosed in U.S. Pat. No. 3,499,591, the entire contents of which are incorporated herein by reference, applies a double row of staples on each side of the incision or the knife cut line. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of staplers are disclosed in U.S. Pat. Nos. 4,429,695, 5,065,929, and 5,156,614, the entire contents of which are incorporated herein by reference.

Electrocautery devices are preferred in certain surgical procedures for effecting improved hemostasis by heating tissue and blood vessels using thermogenic energy, preferably radiofrequency energy, to cause coagulation or cauterization. Monopolar devices utilize one electrode associated with a cutting or cauterizing instrument and a remote return electrode, usually adhered externally to the patient. Bipolar instruments utilize two electrodes and the cauterizing current is generally limited to tissue between the two electrodes of a tissue treating portion (e.g., end effector) of an instrument.

Even though stapling apparatus and electrocauterizing apparatus are respectively generally well suited to control bleeding along the knife cut line, other techniques are herein envisioned for being used in conjunction with these techniques.

Therefore, it is an aspect of the invention to provide a surgical stapling apparatus for providing general hemostasis, tissue joining or welding, and also a wound closure material, for example, for providing additional hemostasis along a cut line formed by a knife or other cutting means and/or along a staple line of the surgical stapling apparatus to reduce or prevent bleeding along the cut line and/or staple line.

SUMMARY

This present disclosure relates to surgical stapling apparatus having a wound closure material applicator for applying a plurality of surgical fasteners to body tissue and dispensing a quantity of wound closure material or components thereof, along a staple line and/or a knife cut line.

According to one aspect of the present disclosure, a surgical stapling apparatus for enhancing one or more properties of body tissue that is or is to be repaired or joined is provided. The surgical stapling apparatus includes a staple anvil positioned on a distal end of the stapling apparatus and having a longitudinal knife track and a staple cartridge positioned adjacent a distal end of the stapling apparatus, the staple cartridge and staple anvil being juxtaposable relative to each other. The staple cartridge includes a plurality of surgical staples individually disposed within individual staple slots formed in rows in the staple cartridge and having a longitudinal knife slot.

The surgical stapling apparatus includes a driving member for firing the surgical staples from the individual staple slots and against the staple anvil, a knife blade structure including a knife blade receivable in and axially movable along the knife track and knife slot, and a wound closure material applicator assembly operatively associated with the stapling apparatus. The wound closure material applicator assembly includes a channel with an orifice, and a conduit in fluid communication with the channel, wherein axial movement of the knife blade structure through the knife track and knife slot axially advances the knife blade structure to permit the orifice to dispense wound closure material from the orifice into an area between the staple anvil and the staple cartridge.

It is envisioned that the applicator assembly further includes at least one reservoir in fluid communication with the conduit, the at least one reservoir containing a wound closure material therein. The driving member can include an actuation sled and the knife blade structure is part of the actuation sled. The knife blade structure preferably includes a needle having the orifice.

The wound closure material can be an astringent, a sulfate of aluminum, an adhesive, a hemostat and/or a sealant.

The reservoir can be compressible. Compression of the reservoir can cause the wound closure material to be dispensed from a needle of the applicator assembly.

The orifice of the needle can be oriented in at least one of a proximal, distal, downward and upward direction. Preferably, the needle has a tip and the orifice is located at the tip. The needle can include a plurality of orifices oriented in at least one of a proximal, distal, downward and upward direction.

The conduit is preferably extendable through at least a portion of the staple cartridge.

The needle can be secured to the knife blade structure. As such, the needle can be adapted to dispense the wound closure material into at least an area near the knife blade and/or into at least an area behind the knife blade.

According to a further aspect of the present disclosure, a surgical stapling apparatus for enhancing one or more properties of body tissue that is or is to be repaired or joined is provided. The surgical stapling apparatus includes a staple anvil positioned on a distal end of the stapling apparatus and having a longitudinal knife track and a staple cartridge positioned adjacent a distal end of the stapling apparatus, the staple anvil and staple cartridge being juxtaposable relative to each other. The staple cartridge includes a working surface, one or more rows of individual staple slots formed in the working surface, a knife slot formed along a length of the working surface, and a plurality of surgical staples individually disposed within the individual staple slots.

The surgical stapling apparatus includes a driving member translatably receivable in the staple cartridge for firing the surgical staples from the individual staple slots and against the staple anvil, the driving member including an actuation sled having a knife operatively connected thereto, the actuation sled being configured and adapted to position the knife to be axially moveable within the track and the knife slot.

The surgical stapling apparatus further includes a wound closure material applicator assembly including an applicator having an orifice and configured to dispense a quantity of wound closure material from the orifice as the knife moves along a length of the knife slot.

The wound closure material applicator can include a needle having an orifice and secured to a portion of the actuation sled, wherein the needle directs the dispensation of wound closure material through the orifice, and a conduit in fluid communication with the needle for delivering the quantity of wound closure material to the needle. The wound closure material applicator assembly can further include a reservoir, containing at least one quantity of wound closure material, in fluid communication with the conduit.

The quantity of wound closure material can be an astringent, an adhesive, a hemostat, and a sealant.

The reservoir can be compressible. Compression of the reservoir causes the wound closure material to be dispensed from the needle of the applicator.

The needle has a tip with the orifice and the tip of the needle is oriented in at least one of a proximal, distal, downward and upward direction. The needle includes a plurality of orifices oriented in at least one of a proximal, distal, downward and upward direction. The orifice is adapted to spray a mist of the wound closure material near and/or behind the knife.

According to a further aspect of the present disclosure, a surgical stapling apparatus for enhancing one or more properties of body tissue that is or is to be repaired or joined, wherein the surgical stapling apparatus includes a staple anvil positioned on a distal end of the stapling apparatus, a staple cartridge positioned adjacent a distal end of the stapling apparatus, the staple cartridge including a working surface defining a knife slot formed along a length thereof, a driving member translatably receivable in the staple cartridge and including an actuation sled having a knife structure operatively connected thereto and positioned within the knife slot, is provided.

The improvement includes a wound closure material applicator assembly configured to dispense a quantity of wound closure material as the knife structure moves along a length of the knife slot.

It is envisioned that the wound closure material applicator includes a needle secured to the actuation sled, wherein the needle directs the dispensation of wound closure material, and a conduit in fluid communication with the needle for delivering the quantity of wound closure material to the needle. It is further envisioned that the needle is secured to the knife.

It is contemplated that the wound closure material applicator further includes a reservoir, containing the quantity of wound closure material, in fluid communication with the conduit.

The quantity of wound closure material is an astringent, an adhesive, a hemostat and/or a sealant.

The reservoir can be compressible. Accordingly, compression of the reservoir causes the wound closure material to be dispensed from the needle. The reservoir can be in the form of a syringe. The syringe can include two chambers each containing a different wound closure material. Alternatively, the syringe includes two chambers each containing a component of a wound closure material, wherein the wound closure material is activated upon combination of the two components of the wound closure material.

It is contemplated that the needle directs wound closure material onto, in front of, behind or to the sides of the knife. It is also contemplated that advantageously, in combination with any of the above aspects of the invention, the conduit can have one or more holes therein to dispense wound closure material onto tissue disposed between the anvil and the cartridge.

Further features of the surgical apparatus of the invention will become more readily apparent to those skilled in the art from the following detailed description of the apparatus taken in conjunction with the drawings.

BRIEF DESCRIPTION OF THE DRAWINGS

Various embodiments of the surgical stapling apparatus of the invention will be described hereinbelow with reference to the drawings wherein:

FIG. 6A is a perspective view of the actuation sled of the disposable loading unit shown in FIG. 5A in a pre-formed condition;

FIG. 6B is a perspective view of the actuation sled shown in FIG. 6A in a formed condition with the knife blade and a dispensing needle of the wound closure material applicator assembly separated therefrom for illustrative purposes;

FIG. 6C is a perspective view of the formed actuation sled shown in FIG. 6B with the knife blade and the dispensing needle mounted to the blade support portion thereof;

FIG. 6D is a perspective view of the dispensing needle and a portion of the conduit in an alternate embodiment;

FIG. 12 is an enlarged perspective view of the actuation channel having an edge for engagement by the hook of the lockout mechanism;

FIGS. 13A and 13B are side views of the lockout mechanism illustrating its movement from a non-engaged to an engaged position;

DETAILED DESCRIPTION OF PREFERRED EMBODIMENTS

Figure 1A:
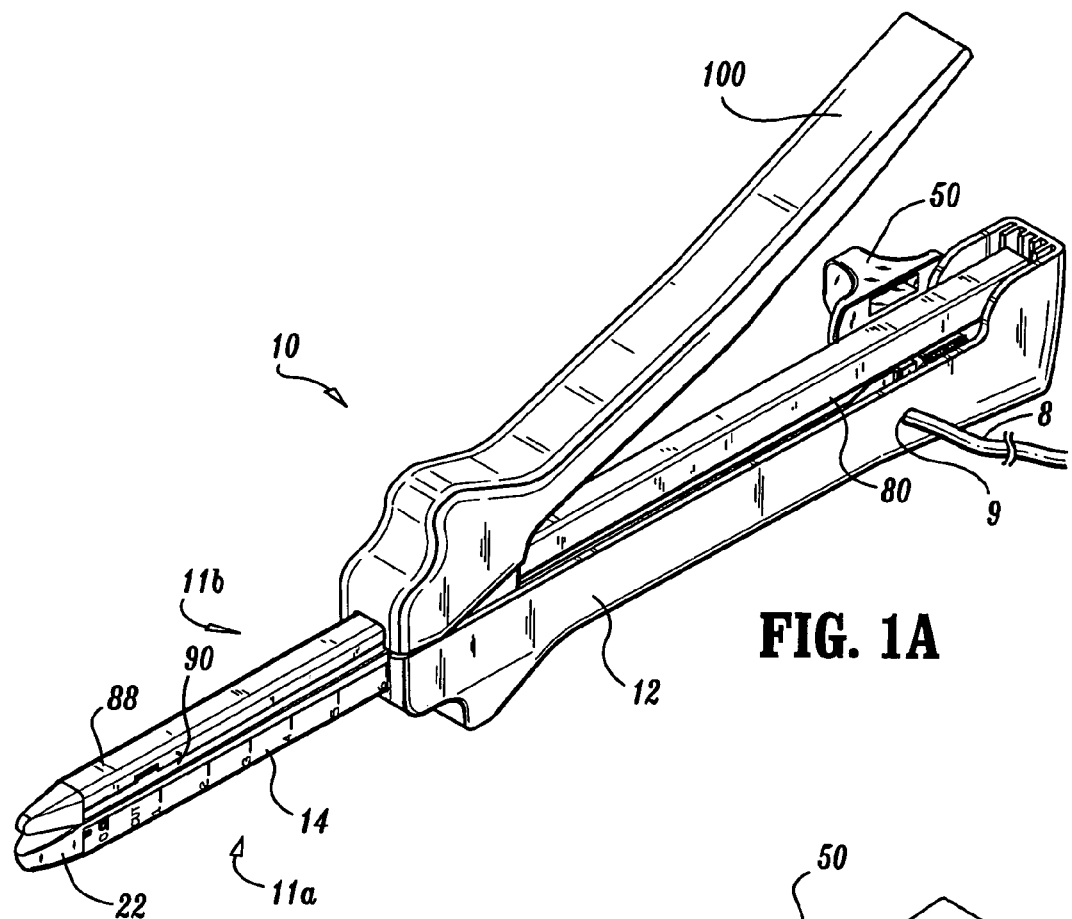
FIG. 1A is a perspective view of a surgical stapling apparatus having a wound closure material applicator assembly constructed in accordance with a preferred embodiment, with the clamping handle of the apparatus disposed in an upright open position.

Preferred embodiments of the presently disclosed surgical stapling apparatus will now be described with reference to the drawing figures wherein like reference numerals identify similar or identical elements. In the drawings and in the following description, the term "proximal", as is traditional, will refer to the end of the apparatus which is closer to the operator, while the term "distal" will refer to the end of the apparatus which is further away from the operator.

The present invention provides a surgical stapling apparatus having a wound closure material applicator assembly which applies at least one biological and/or synthetic biocompatible sealant, hemostat, adhesive, and combinations thereof (individually or collectively referred to herein as wound closure material), as well as surgical fasteners or staples, for example, for providing hemostasis, tissue joining or welding. The application of a wound closure material to the cut line and/or staple line can provide short, i.e., temporary, and long-term, i.e., permanent, hemostasis and sealing, and reduce or prevent bleeding along a knife cut line and/or staple line, while the stapling features provide short and long-term tissue strength and hemostasis.

Since knife cut line and staple line bleeding is reduced or prevented, the surgical stapling apparatus of the present invention makes it possible to expand the applicable range of specific staple sizes to include thinner or thicker staples used in highly vascularized tissue. For example, it is contemplated that relatively large-size staples could be used with the surgical stapling apparatus of the present invention to join thin, highly vascularized tissue.

Figure 1B:
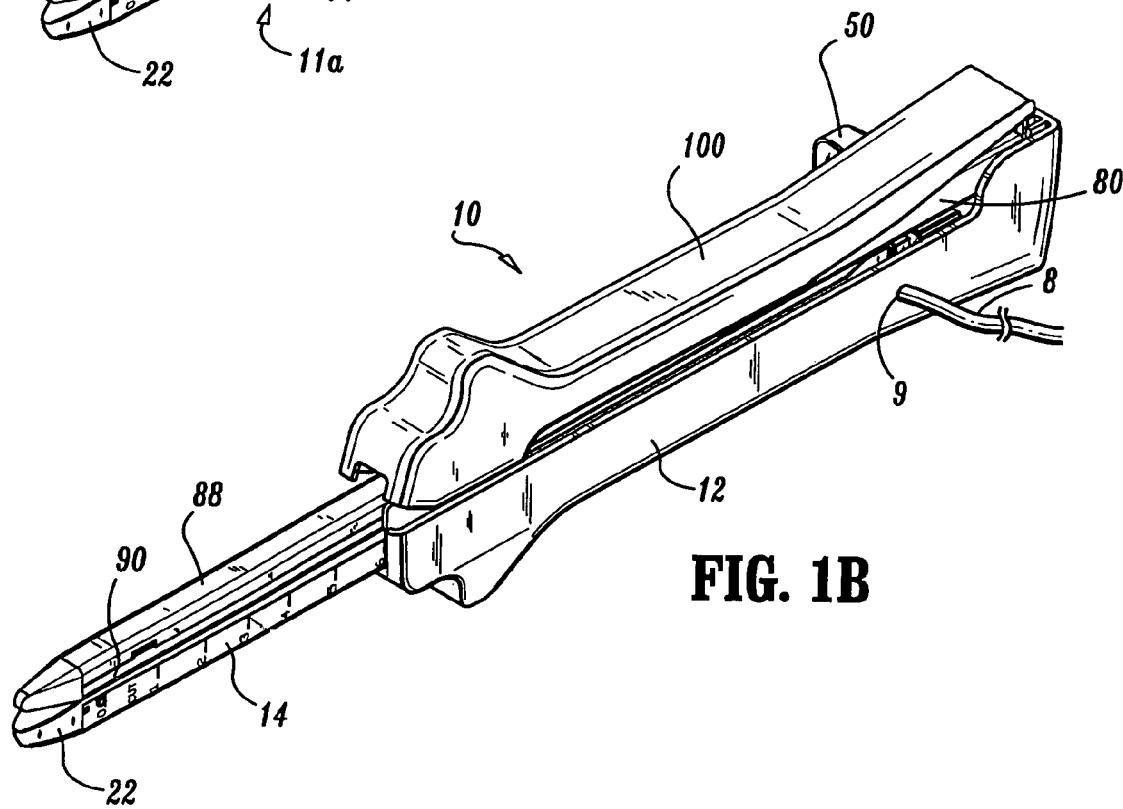
FIG. 1B is a perspective view of the surgical stapling apparatus illustrated in FIG. 1A with the clamping handle disposed in a closed position.

Referring now to the drawings wherein like reference numerals identify similar structural elements, there is illustrated in FIGS. 1A and 1B a surgical stapling apparatus in accordance with a preferred embodiment and designated generally as reference numeral 10. Surgical stapling apparatus 10 includes a cartridge half-section 11a and an anvil half-section 11b.

Figure 2A:
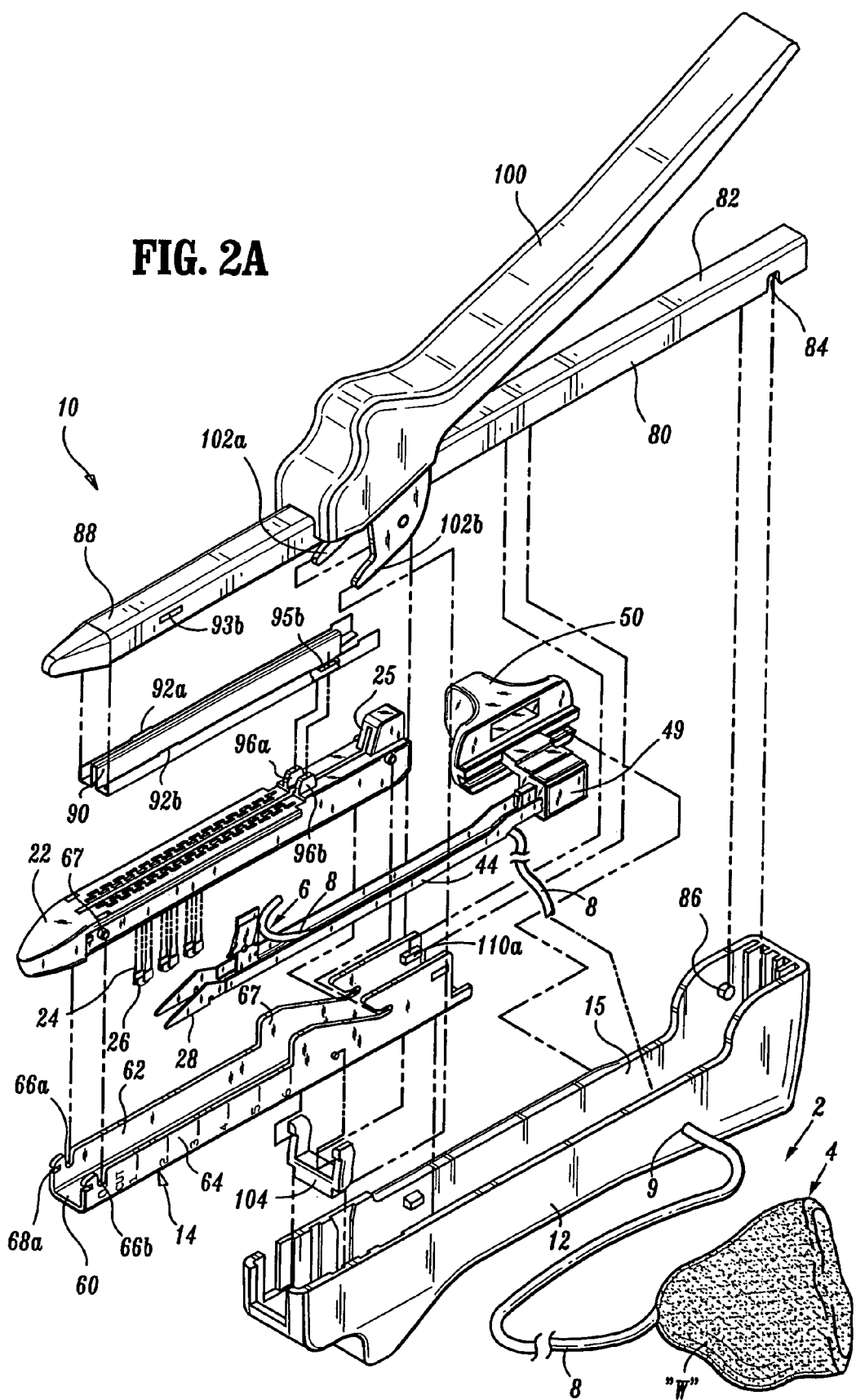
FIG. 2A is an exploded perspective view of the surgical stapling apparatus of FIG. 1A.
Figure 2B:
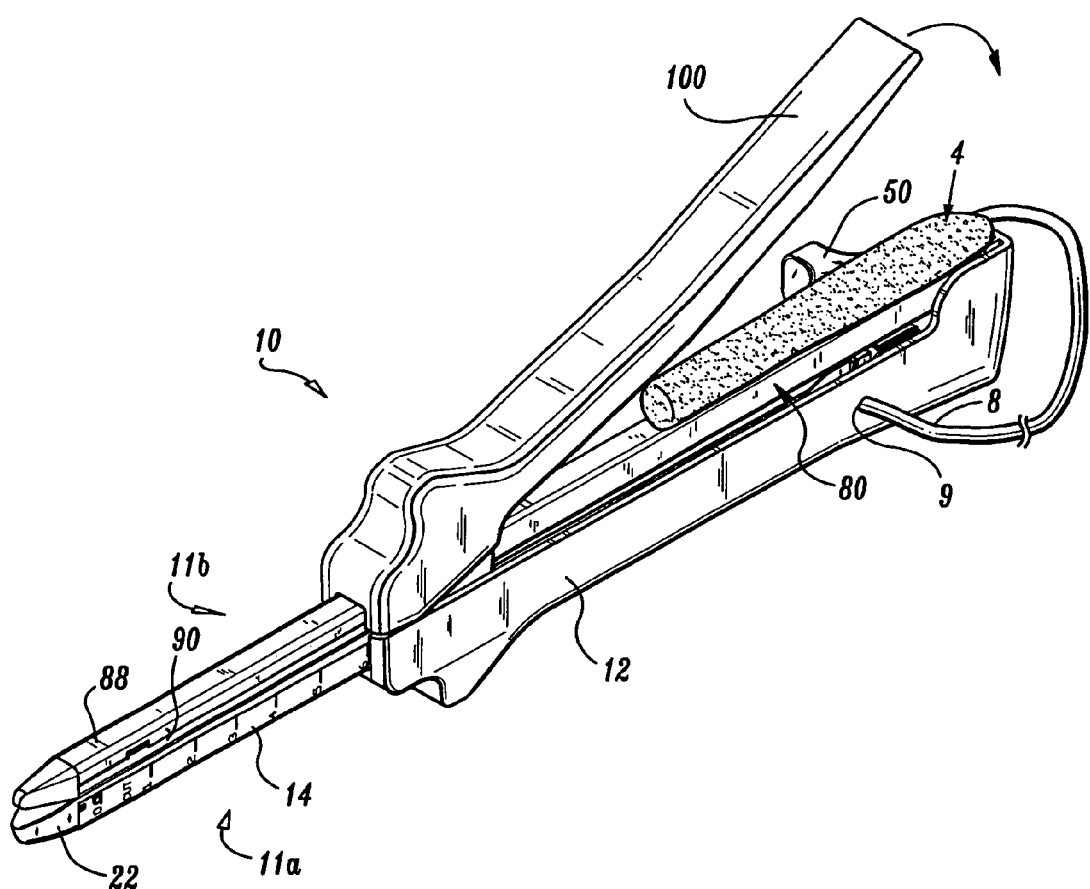
FIG. 2B is a perspective view of a surgical stapling apparatus having a wound closure material applicator assembly constructed in accordance with another preferred embodiment.
Figure 3:
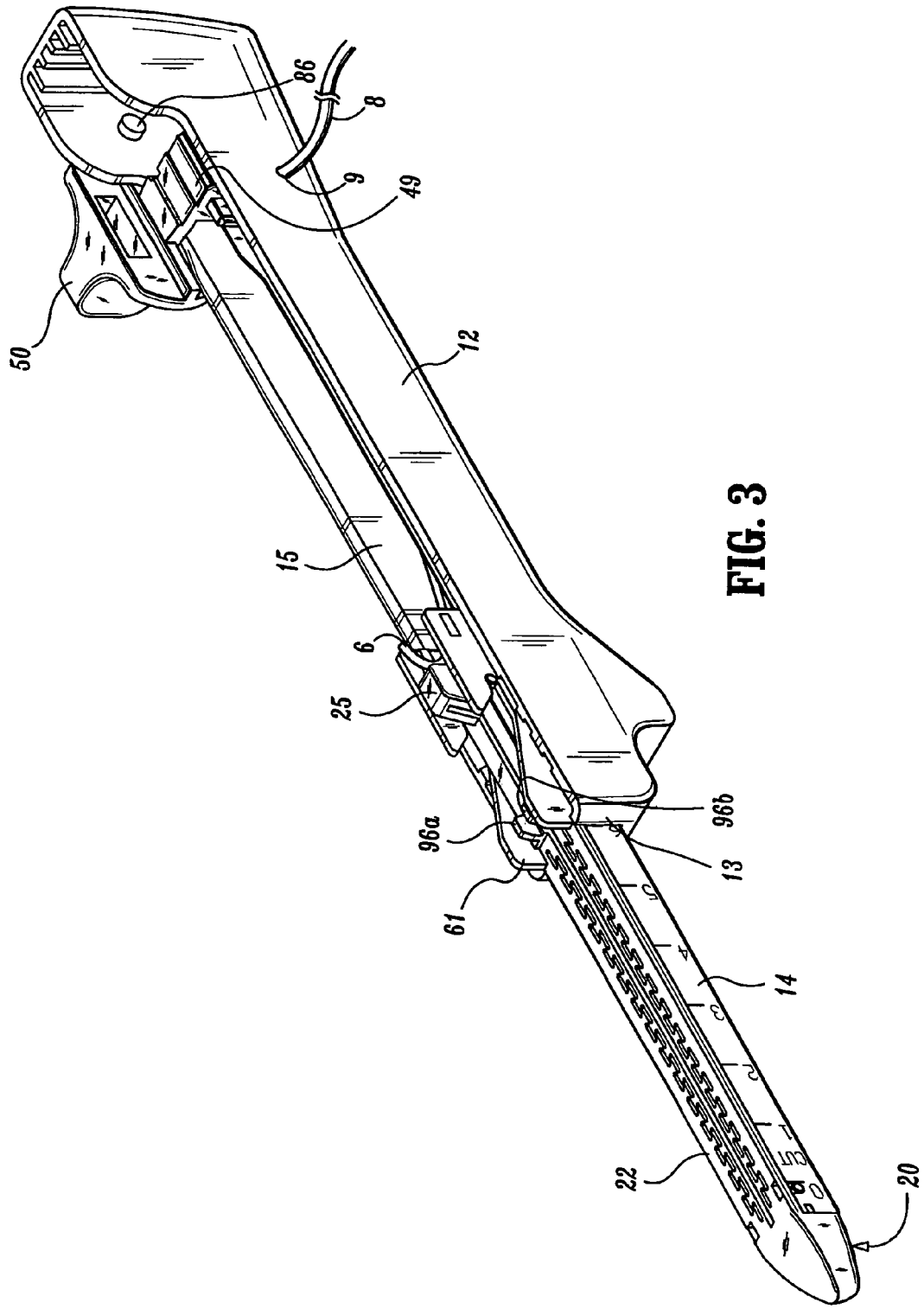
FIG. 3 is a perspective view of a cartridge half-section of the surgical stapling apparatus of FIG. 1A.
Figure 4A:
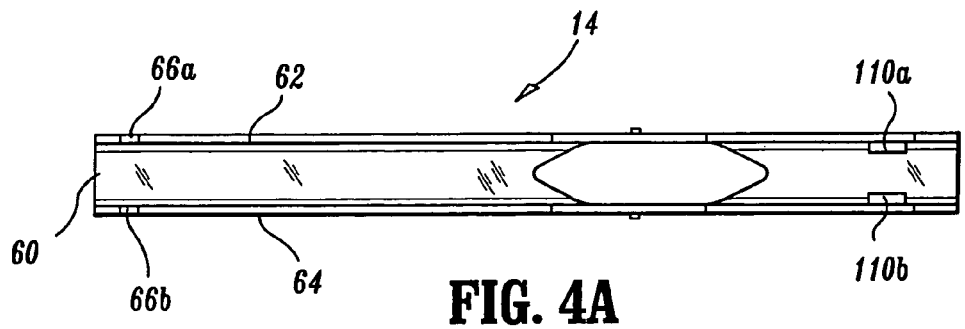
FIG. 4A is a top plan view of a retention channel of the surgical stapling apparatus of FIG. 1A.
Figure 4B:
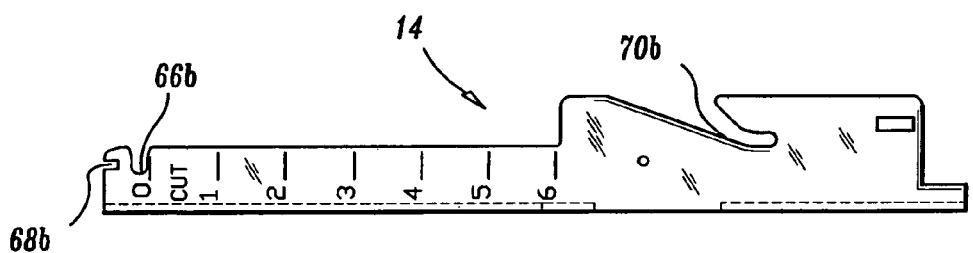
FIG. 4B is a side elevational view of the retention channel shown in FIG. 4A.
Figure 4C:
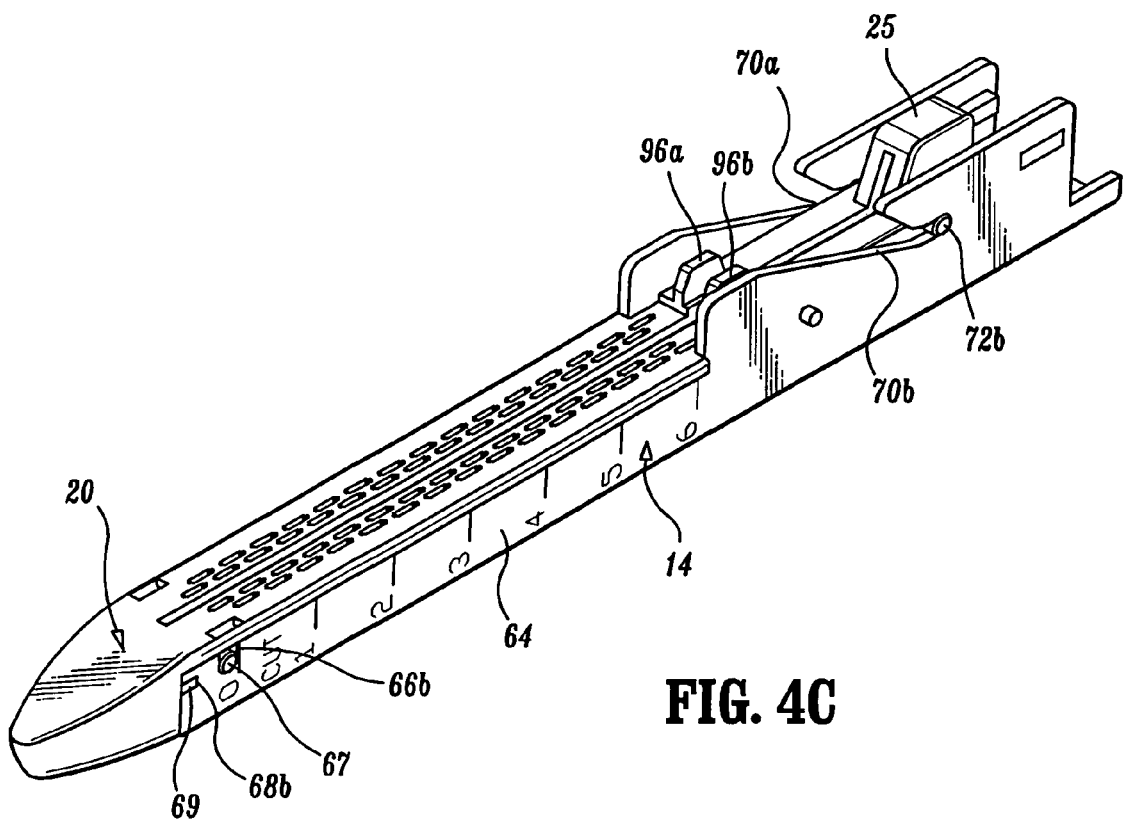
FIG. 4C is a perspective view of the retention channel of FIGS. 4A and 4B with the disposable loading unit retained therein.

Referring to FIGS. 2A, 2B and 3, stapling apparatus 10 includes a body portion 12 defining a handle for grasping and supporting stapling apparatus 10. A retaining channel 14 is mounted in an interior cavity 15 of body portion 12 adjacent the distal end thereof. Retaining channel 14 is dimensioned and configured to support a disposable loading unit 20, as illustrated in FIG. 4C.

Figure 5A:
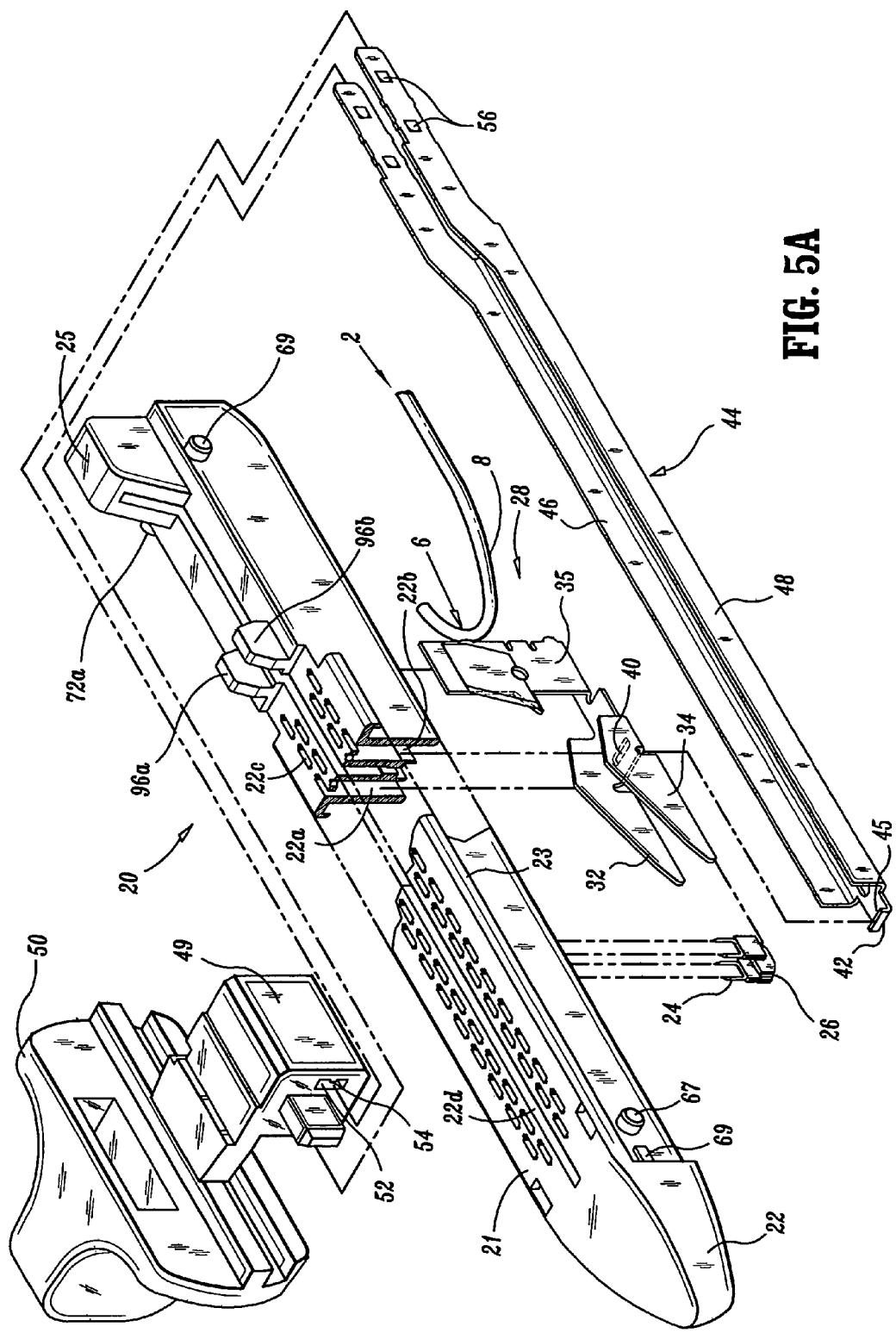
FIG. 5A is an enlarged perspective view, with parts separated, of the disposable loading unit and actuation assembly of the surgical stapling apparatus of FIG. 1A.

As shown in FIG. 5A, disposable loading unit 20 includes a cartridge 22 having tissue contacting or working surface 21, a plurality of slots 22c which support a corresponding is number of surgical staples 24, a plurality of staple pushers or ejectors 26 adapted and configured to eject staples 24 from slots 22c when acted upon by a staple driving force, and an actuation sled 28 which is mounted to translate through cartridge 22 in a longitudinal direction to transmit a staple driving force to ejectors 26 and dispense a quantity of wound closure material to be a target surgical site.

As seen in the figures, particularly in FIGS. 2A, 3, and 5A, surgical stapling apparatus 10 includes a wound closure material applicator assembly 2 operatively associated with surgical stapling apparatus 10. Wound closure material applicator assembly 2 includes a compressible (or syringe-like, etc.) reservoir 4 (see FIG. 2A) in fluid communication with a needle 6 via a conduit 8. In use, wound closure material applicator 2 manually or automatically supplies a wound closure material "w", or a component thereof, to a target surgical site. Conduit 8 enters body portion 12 via an opening 9 and is configured for traversing approximately the entire length of body portion 12 and cartridge 22, during firing of apparatus 10. Preferably, a distal portion of conduit 8 is supported by actuation sled 28 and needle 6 is secured to, connected to, or otherwise mounted on a portion of actuation sled 28, here on knife blade 36, in such a manner that the tip of needle 6 is oriented in a proximal direction. Conduit 8 preferably has sufficient slack to extend along the entire path of knife blade 36 for applying wound closure material "W" along the entire or substantially the entire length of a knife cut line formed by knife blade 36 (see FIG. 16).

Reservoir 4, in one embodiment, is compressible and configured for placement between cartridge half-section 11a and anvil half-section 11b of apparatus 10. In this manner, as lever handle 100 is moved towards body portion 12 (see FIG. 2B) reservoir 4 is compressed. Compression of reservoir 4 causes wound closure material "W" contained therein to be urged through conduit 8 and dispensed from needle 6. Preferably, wound closure material "W" is dispensed during the staple firing procedure so that wound closure material "W" is dispensed along the length of the staple line and/or knife cut line.

Figure 2C:
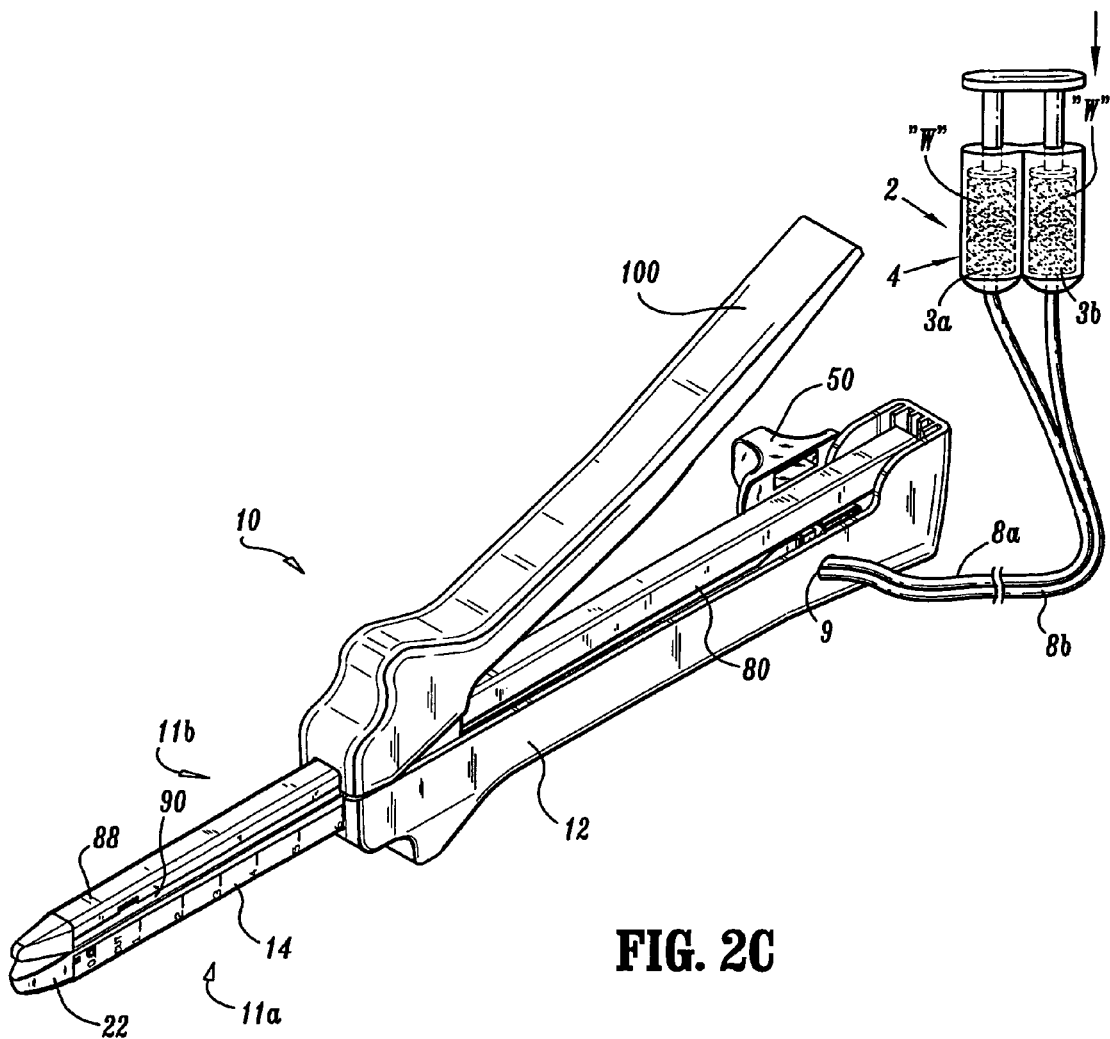
FIG. 2C is a perspective view of a surgical stapling apparatus having a wound closure material applicator assembly constructed in accordance with another preferred embodiment.

In another embodiment, as shown by FIG. 2C, wound closure material applicator assembly 2 includes two reservoirs 3a, 3b, e.g., two syringe-type non-compressible reservoirs, each in fluid communication with dispensing needle 6 (not shown) via at least one respective conduit 8a, 8b. First reservoir 3a stores one component of wound closure material "W" and second reservoir 3b stores a second component of wound closure material "W". Preferably, the first and second reservoirs 3a, 3b are identical for encasing an equal or appropriate volumetric amount of their respective component as compared to the other reservoir to maintain a predetermined desired ratio of the first component to the second component, which is typically a 1:1 ratio. Reservoirs 3a, 3b are preferably actuated manually for dispensing their respective component. Alternatively, depending on the components and situation, the two components can be joined and fed through a common conduit.

Preferably, wound closure material "W" is formed by the two components is fibrin glue or fibrin sealant, which acts as a hemostatic agent and as a tissue adhesive. Fibrin sealant is formed by the rapid polymerization, which occurs when a solution of proteomic clotting factors, such as fibrinogen, comes into contact with a solution of a proteomic catalyst, such as thrombin. This rapid polymerization typically commences within two seconds after the solutions initially contact one another, and it typically attains a soft set within ten seconds of contact. Because of the rapid polymerization upon intimate interaction of fibrinogen and thrombin, it is important and preferable to maintain these two blood proteins separate until applied at the application site. Accordingly, it is preferred that wound closure material applicator assembly 2 supplies each blood protein separately from the other blood protein by using a separate conduit for each protein.

It is envisioned that wound closure material "W" can include one or a combination of adhesives, hemostats, sealants. Surgical biocompatible wound closure materials which can be employed in or applied the surgical instruments, especially surgical staplers, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials under sold the trade designations CoStasis™ by Tyco Healthcare Group, LP, and Tisseel™ sold by Baxter International, Inc. Hemostats herein include astringents, e.g., aluminum sulfate, and coagulants.

Figure 5B:
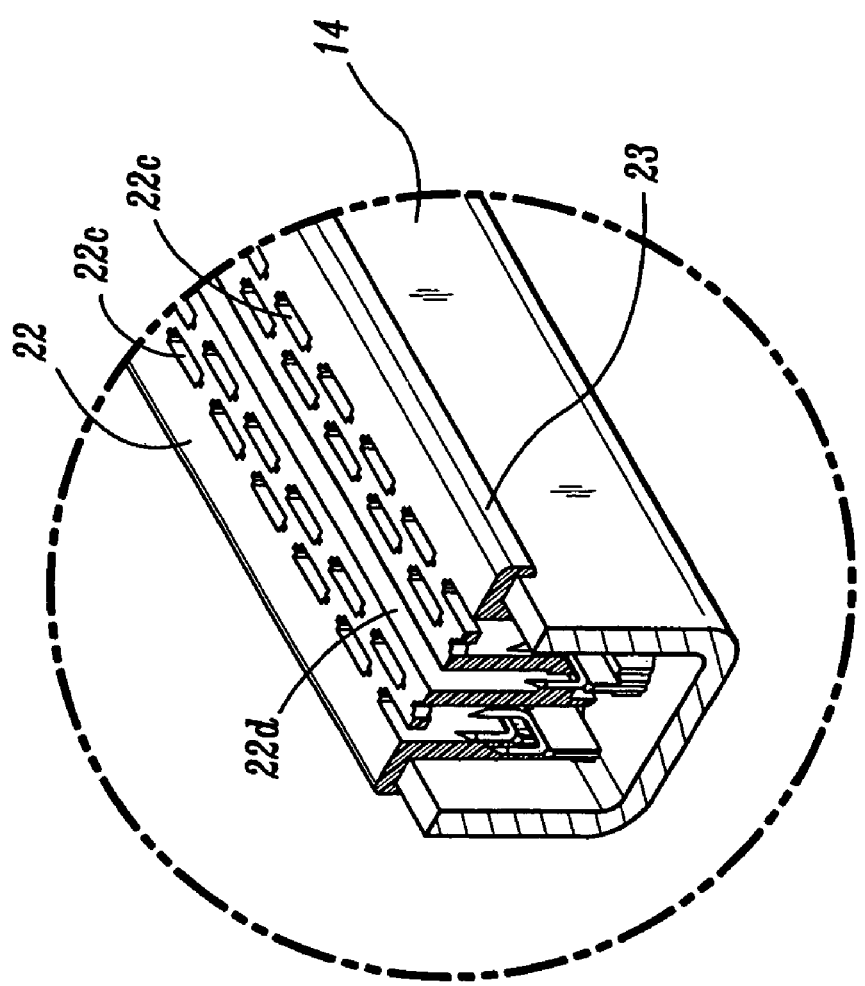
FIG. 5B is a cross-sectional view of the indicated area in FIG. 5A showing the engagement of the cartridge lip and the retention channel.

Cartridge 22 is preferably fabricated from liquid crystal polymer material, such as liquid crystal polymer resin, commercially available from Plasticsnet.com under the trademark Xydar, although other materials are contemplated. Cartridge 22 has a lip 23 which engages the retention channel 14 to prevent inward rotation of cartridge 22 (see FIG. 5B).

As best seen in FIG. 6A, actuation sled 28 is preferably monolithically formed from a single piece of sheet metal which is folded into the desired structural configuration shown in FIGS. 6B and 6C. In this configuration, actuation sled (staple actuator) 28 defines a base portion 30, two upstanding cam wedges 32 and 34, and an upstanding shank 35 which supports the knife blade 36 and the distal portion of conduit 8. Conduit 8 and knife blade 36 are preferably spot welded to shank 35, although other known fastening methods, e.g., clamping, may be employed. As illustrated in FIG. 6B, a weldment port 37 and a winglet 39 are provided to facilitate the proper alignment and cohesion of knife blade 36 to shank 35 during fabrication. Actuation sled 28 can also be non-monolithically formed. Needle 6 is preferably formed to have a generally semi-circular configuration (shown in FIGS. 6B, 6C) where it has an arc, or radius of curvature, that is about 180°. Alternatively, in another embodiment, needle 6 is formed to have an arc, or radius of curvature, that is about 270° (see FIG. 6D).

Cam wedges 32 and 34 are staggered with respect to one another so that one leads the other throughout the sled's translation through cartridge 22. Longitudinal slots 22a and 22b accommodate the longitudinal translation of cam wedges 32 and 34, while a slot, or knife slot 22d (see FIGS. 5A and 5B), i.e., knife track, accommodates the longitudinal translation of shank 35.

Base portion 30 of actuation sled 28 has a transverse slot 40 defined therein which is dimensioned and configured to releasably retain an upturned flange 42 formed at the distal end of elongated actuation channel 44 (FIG. 5A). When disposable loading unit 20 is placed into retaining channel 14 and actuation sled 28 is disposed in its proximal-most position, flange 42 releasably engages slot 40. Thus, movement of actuation channel 44 moves actuation sled 28. After a stapling operation, when disposable loading unit 20 is removed from retaining channel 14, flange 42 is easily disengaged from slot 40.

With continued reference to FIG. 5A, actuation channel 44 is defined by a base portion 45 and two parallel upstanding beams 46 and 48 of elongate configuration. The distal ends of beams 46 and 48 are staggered to match the staggered orientation of cam wedges 32 and 34, respectively. The proximal end of each beam projects rearwardly to engage a mounting block 49 that is associated with a firing knob 50. A pair of slots 52 (only one of which is shown) is formed in mounting block 49 for receiving the proximal end of each of the upstanding beams 46, 48 of actuation channel 44 and slots 52 are provided with detents 54 for engaging apertures 56 in the beam ends to lockingly retain beams 46, 48 in mounting block 49. In use, longitudinal movement of firing knob 50 causes corresponding longitudinal translation of actuation channel 44 and actuation sled 28.

Referring to FIGS. 2A and 4C, retention channel 14 includes a base portion 60 and two upstanding parallel walls 62 and 64. Numerical indicia are imprinted on the walls 62, 64 of retention channel 14 to indicate the length of the staple line. Retention structures in the form of retention notches 66a, 66b are provided at the distal end of each of walls 62, 64 to engage corresponding structures in the form of protuberances 67 provided on disposable loading unit 20. Similarly, slots 68a and 68b are provided at the distal end of each of walls 62, 64 for engaging corresponding detents, such as detent 69 provided on disposable loading unit 20. These structures inhibit lateral, longitudinal and perpendicular shifting of cartridge 22 (and disposable loading unit 20) within retaining channel 14. Ramped engagement slots 70a and 70b are also defined in the opposed walls of retention channel 14 for interacting with a pair of opposed protuberances 72a and 72b of disposable loading unit 20 (FIG. 5A) to guide disposable loading unit 20 into retention channel 14 when loaded into the surgical stapling apparatus 10.

Referring again to FIG. 2A, surgical stapling apparatus 10 further includes an elongate anvil support beam 80 which has a generally U-shaped cross-sectional configuration. Proximal end portion 82 of support beam 80 has a notched area 84 for engaging a pair of corresponding detents 86 (only one of which is shown), which extend into cavity 15 of body portion 12 adjacent the proximal end thereof. Detents 86 are engaged when cartridge half-section 11a and anvil half-section 11b are mated with one another. Distal end portion 88 of anvil support beam 80 is configured to support a preformed anvil plate 90 against which staples 24 are driven and formed during a stapling procedure.

Figure 7:
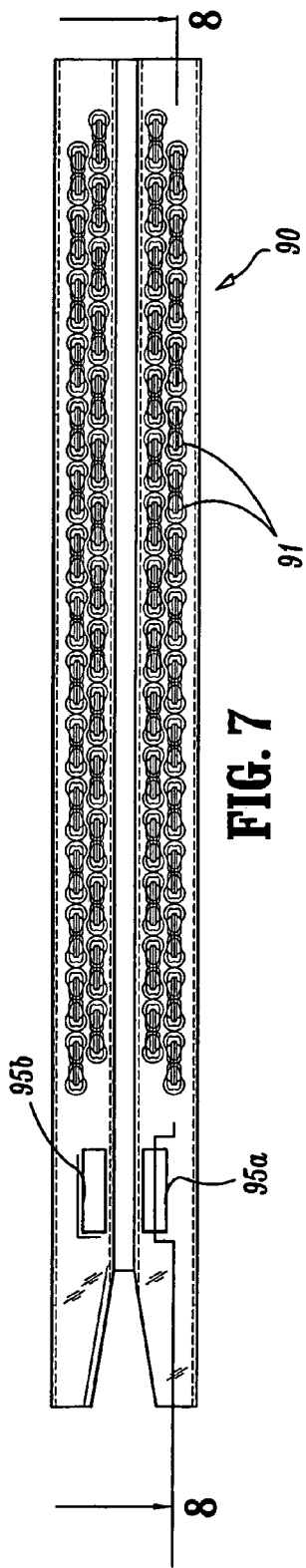
FIG. 7 is a plan view of the preformed anvil plate which is mounted to the anvil support beam of the anvil half-section of the surgical stapling apparatus shown in FIG. 1A.
Figure 8:
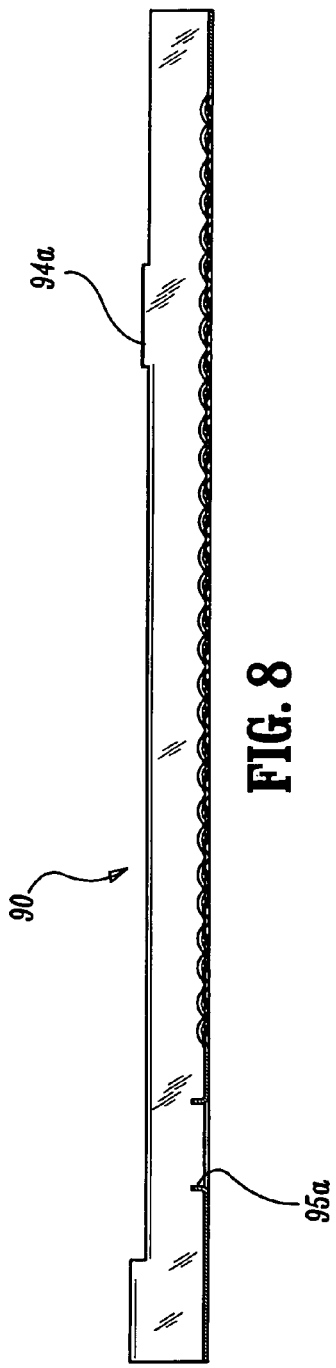
FIG. 8 is a cross-sectional view of the preformed anvil plate taken along line 8-8 of FIG. 7.
Figure 9:
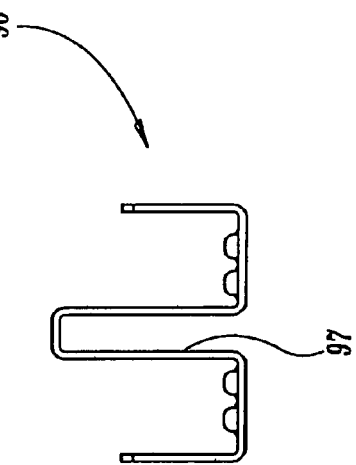
FIG. 9 is a front end view of the preformed anvil plate illustrated in FIGS. 7 and 8.
Figure 10:
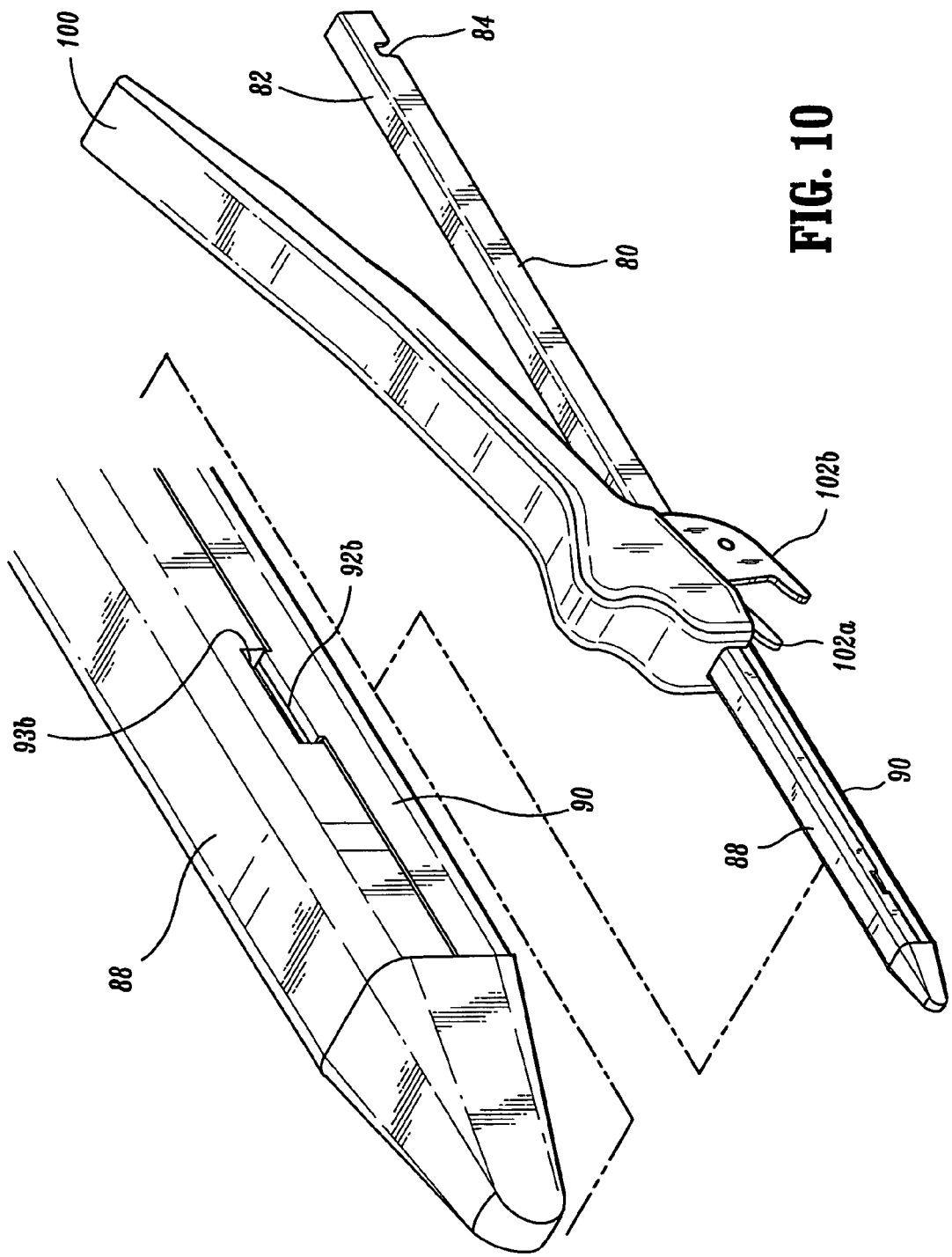
FIG. 10 is a perspective view of the anvil half-section of the surgical stapling apparatus of FIG. 1A with an enlarged localized view of a distal portion thereof illustrating the connective engagement between the anvil plate and the anvil support beam.

Referring to FIGS. 7 and 8, anvil plate 90 can be formed from a unitary piece of metal and cold formed and stamped to define a plurality of staple forming recesses or cups 91. Each staple forming recess 91 corresponds to a particular staple housed within cartridge 22. Anvil plate 90, as shown in FIG. 2A, is provided with two opposed tangs 92a and 92b which extend inwardly to engage complementary engagement slots 93b (only one is shown) in anvil support beam 80 during fabrication and assembly (see FIG. 10). The cross-sectional configuration of anvil plate 90 is dimensioned to complement the cross-sectional geometry of support beam 80 (see FIG. 9). More particularly, a cavity, or knife track 97, which extends along the length of anvil plate 90, corresponds to a similar channel formed in support beam 80. These areas accommodate shank 35 (see FIGS. 6A-6C), and knife blade 36 and needle 6 as they translate distally to form an incision in stapled body tissue during a stapling operation.

A pair of rectangular apertures 95a and 95b are formed in anvil plate 90 adjacent the proximal end thereof for receiving a pair of correspondingly positioned flanges or projections 96a and 96b which project upwardly away from the tissue contacting surface (see FIGS. 2 and 4C). The interaction between aperture 95a, 95b and flanges 96a, 96b ensures that cartridge 22 and anvil plate 90 are properly aligned with one another during a stapling procedure. Flanges 96a, 96b are spaced proximally of tissue stop portion 61 of retention channel 14. Portion 61 and distal edge 13 of body portion 12, best seen in FIG. 3, cooperate to prevent tissue from extending proximally.

Referring again to FIGS. 2A and 2B, anvil half-section 11b of stapling apparatus 10 further includes clamping handle 100 which is used to securely clamp tissue between the staple forming surface of anvil plate 90 and tissue contacting surface 21 of cartridge 22 (see FIG. 5A). Clamping handle 100 is pivotably mounted to anvil support beam 80 about a transverse pivot pin, which is not shown in the drawings. A pair of clamping hooks 102a and 102b depend from clamping handle 100 for interacting with U-shaped clamping beam 104 supported within the internal cavity defined in body portion 12.

When apparatus 10 is assembled prior to use, notched area 84 at proximal end 82 of anvil support beam 80 is engaged with cooperating detents 86 in inner cavity 15 of body portion 12. Thereupon, anvil half-section 11b is mated with cartridge half-section 11a, and clamping handle 100 is disposed in the upright unclamped position shown in FIG. 2B. Subsequently, when body tissue is disposed between the staple forming surface of anvil plate 90 and tissue contacting surface 21 of cartridge 22 (see FIG. 5A), anvil half-section 11b is pivoted towards cartridge half-section 11a, about the detents in body portion 12, such that the distal ends of clamping hooks 102a and 102b are positioned immediately adjacent the proximal end of the base of U-shaped clamping beam 104. Concomitantly, flanges 96a and 96b engage apertures 95a and 95b in anvil plate 90 to ensure proper alignment of the anvil and the cartridge.

Then, to securely clamp the captured body tissue, clamping handle 100 is pivoted from the position illustrated in FIG. 1A to that which is shown in FIG. 1B. At such a time, clamping hooks 102a and 102b engage the base of clamping beam 104, locking surgical stapling apparatus 10 in a clamped condition. During clamping, the captured body tissue exerts a counter-force against the tissue contacting surface of cartridge 22 and the fastener forming surface of the anvil plate 90, urging the two structures apart. To overcome these forces and prevent the proximal portion 82 of anvil support beam 80 from bending, bearing surfaces are defined within retention channel 14 to support the compressive forces generated during clamping. In particular, as illustrated in FIG. 4A, opposed bearing shelves 110a and 110b are stamp formed in opposed walls 62 and 64 of retention channel 14. The bearing shelves are positioned to abut the medial section of anvil support beam 80 proximate the clamping handle pivot point.

Figure 11:
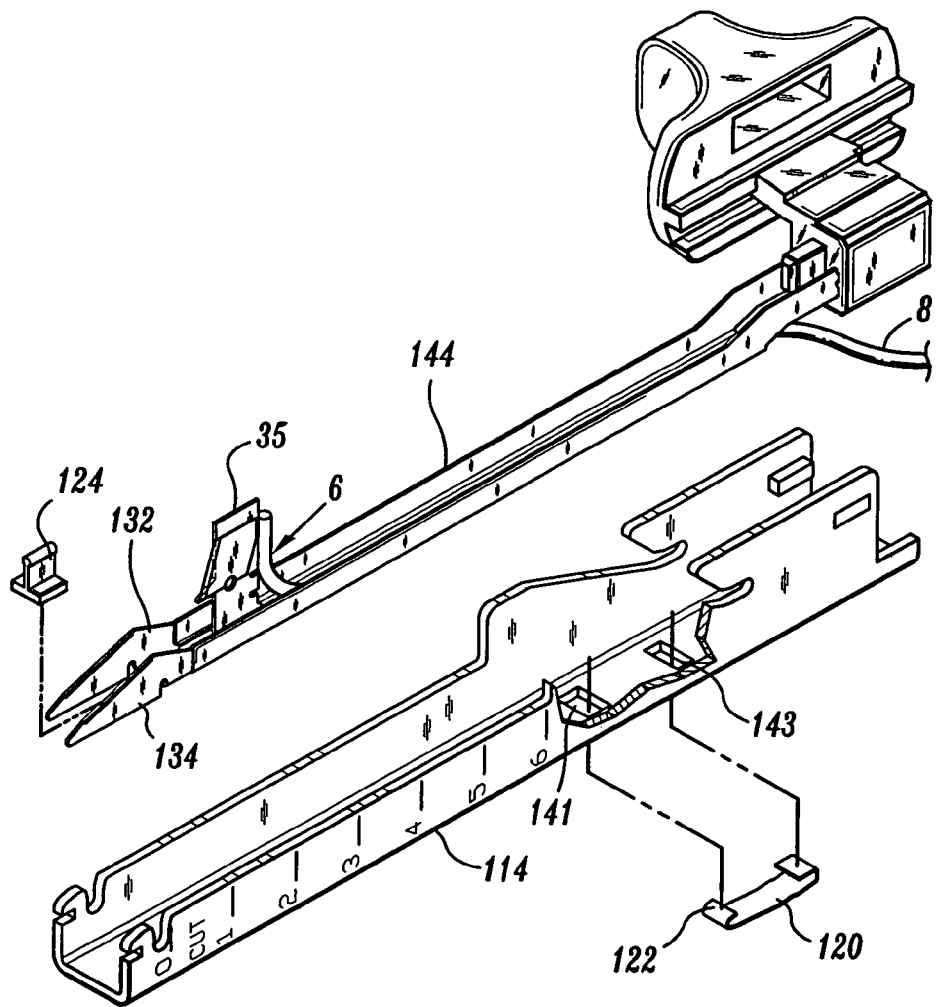
FIG. 11 is an exploded perspective view of a lockout mechanism to prevent reactuation of the apparatus.
Figure 11A:
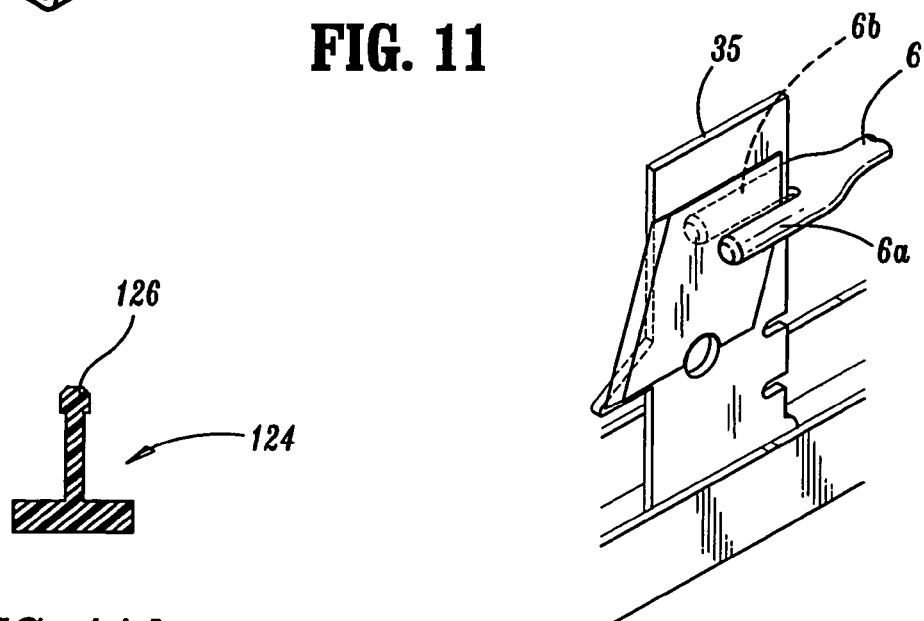
FIG. 11A is an enlarged cross-sectional view of the T-shaped member of the lockout mechanism.
Figure 11B:
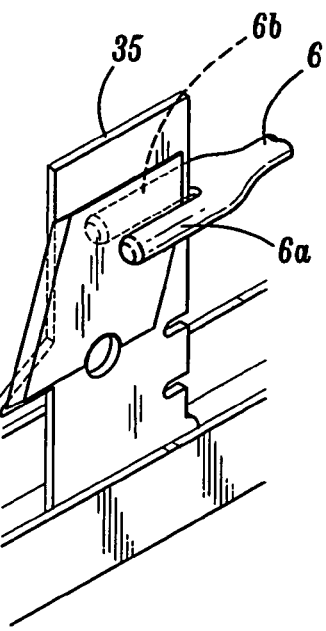
FIG. 11B is a perspective view of the needle and the shank according to an alternate embodiment of the present disclosure wherein the needle is forked with two tines and each tine is directed to an opposing side of the shank.

It may also be desirable to provide a locking mechanism to prevent reactuation of the apparatus after it has been actuated. For example, a locking member 120 shown in FIG. 11 can be positioned in retaining channel 114. Locking member 120 is biased to an upward engagement position and each end extends through a window 141, 143 in channel 114. A T-shaped member 124 is positioned between cam wedges 132, 134 to bias the hook portion 122 out of engagement with actuation channel 144. Head portion 126 of T-shaped member 124 (FIG. 11A) is initially retained in the cartridge by a pair of detents in the cartridge which extend into the knife slot. When the apparatus is actuated, head portion 126 of T-shaped member 124 is in the knife slot. Needle 6 preferably is formed to have an angle of about 90° with respect to the bottom surface of actuation channel 144 (FIG. 11). Further still, it is contemplated that needle 6 could be disposed to each of the sides of the shank, as shown in FIG. 11B. Preferably, needle 6 has a forked configuration with a pair of tines 6a, 6b where each tine 6a, 6b is directed towards an opposing side of shank 35.

A second pair of detents (not shown) at the distal end of the knife slot engages head portion 126 of T-shaped member 124 to hold it at the distal end of cartridge 122 when cam wedges 132, 134 are advanced to the distal position. When actuation channel 144 is retracted from the post-actuated position to the pre-actuated position, T-shaped member 124 remains forward allowing hook portion 122 to return to the upward position and extend through the window 141 in retaining channel 114 to engage edge 143 (see FIGS. 12 and 13A) of actuation channel 144 to prevent advancement of the actuation channel.

FIGS. 13A and 13B illustrate movement of the locking member 120 from an initial non-engaged position (FIG. 13A) out of engagement with actuation channel 144 to an engaged position (FIG. 13B) in engagement with actuation channel 144 to prevent distal movement thereof.

Figure 14:
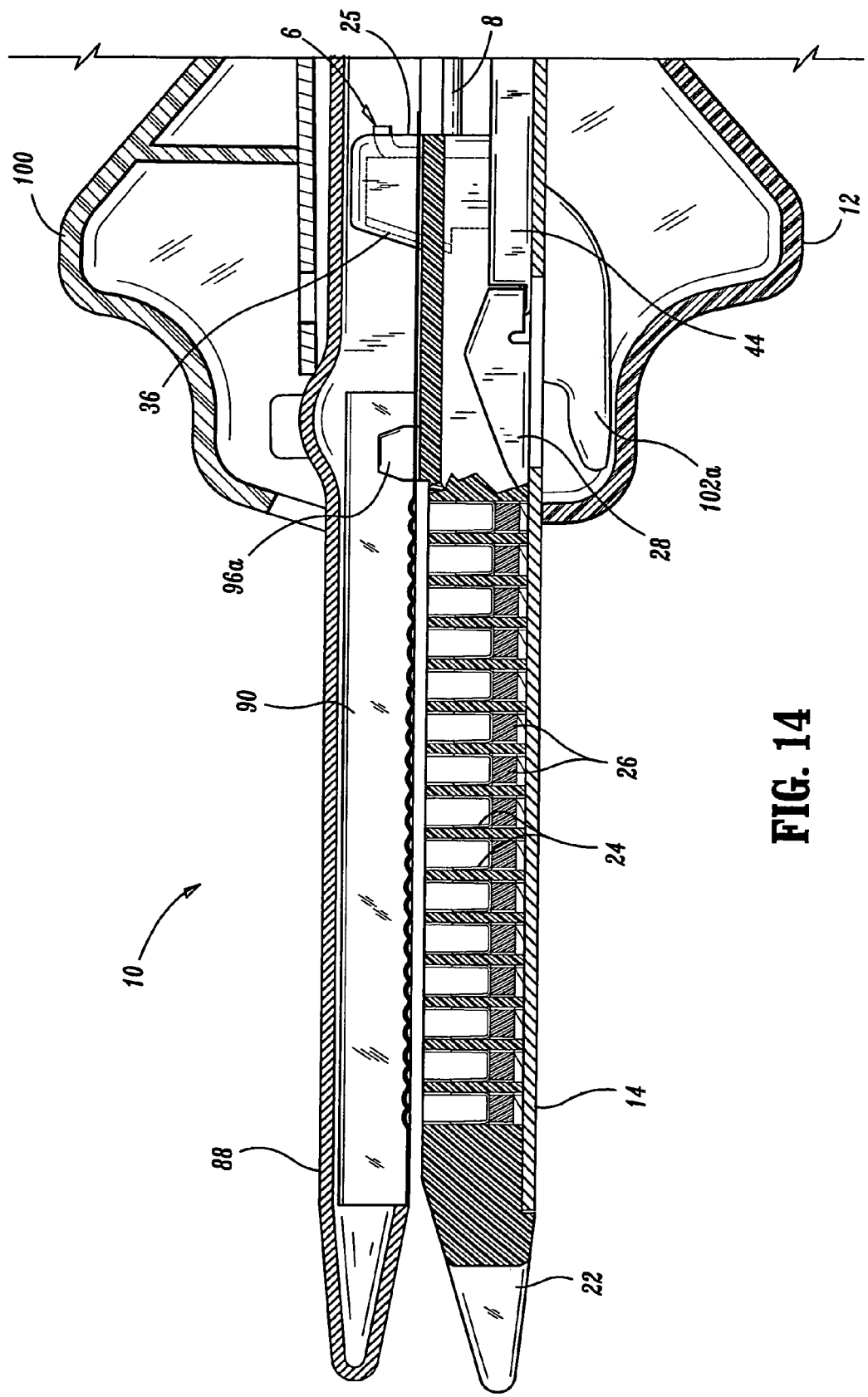
FIG. 14 is a side elevational view in cross-section of the surgical stapling apparatus of the present invention with the actuation sled supporting the adhesive dispensing needle and disposed in a pre-actuated proximal position.
Figure 15:
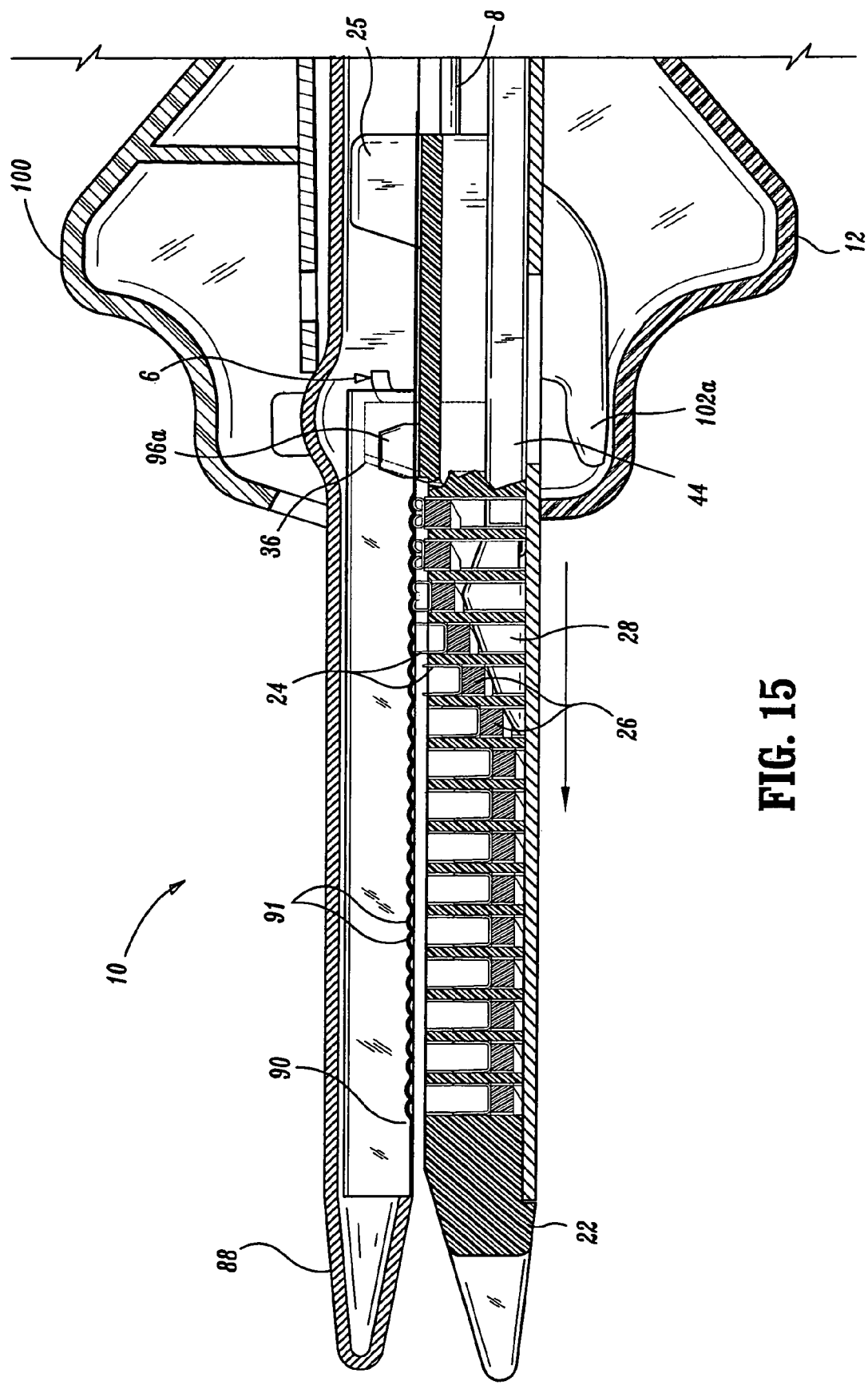
FIG. 15 is a side elevational view in cross-section of the surgical stapling apparatus of the present invention with the actuation sled disposed in a partially advanced position.
Figure 16:
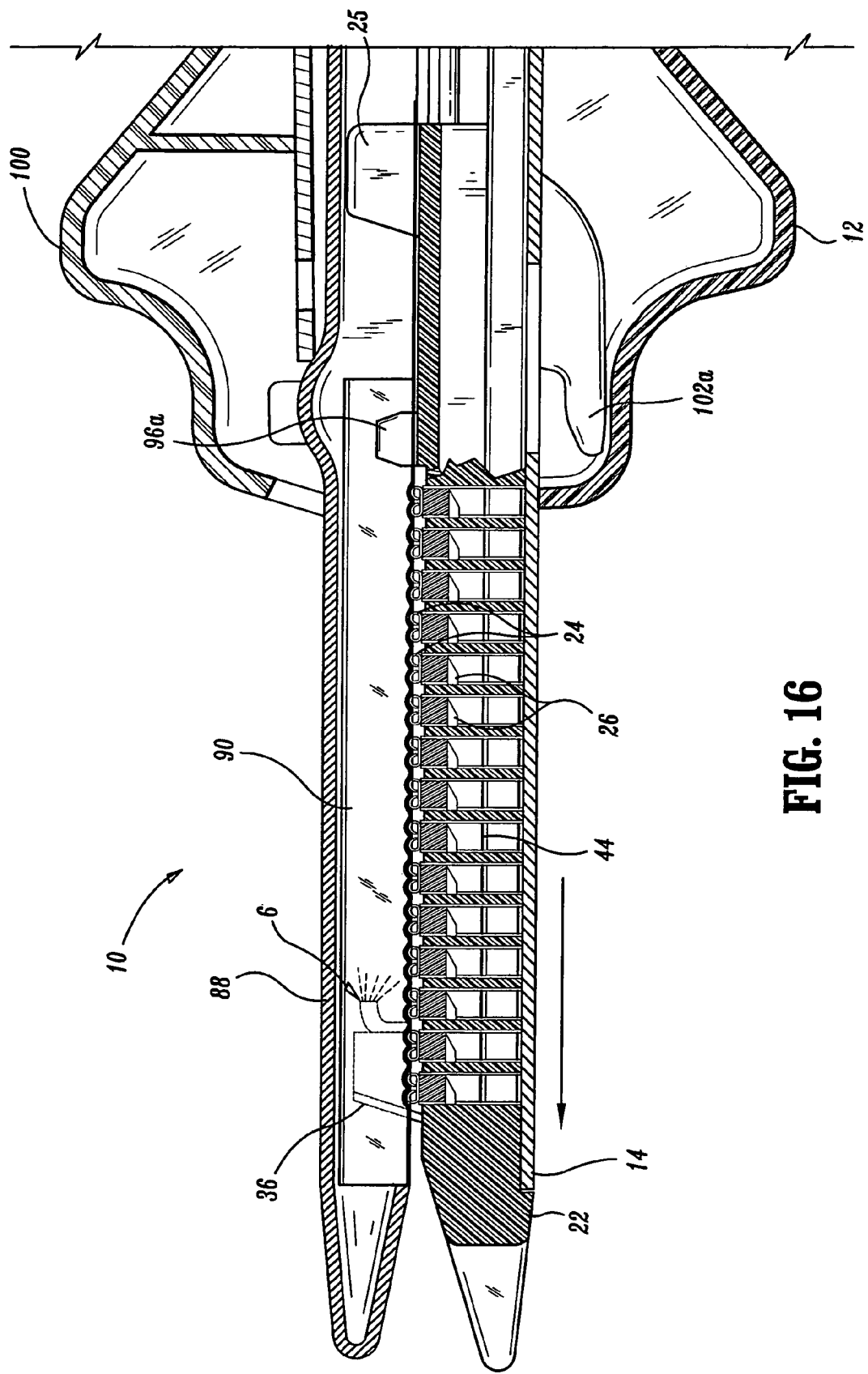
FIG. 16 is a side elevational view in cross-section of the surgical stapling apparatus of the subject application with the actuation sled advanced to the distal end of the cartridge at the conclusion of a staple firing procedure.

Referring now to FIGS. 14-16, there is illustrated, in sequential order, a staple firing operation in which a plurality of staples are ejected from cartridge 22 and driven against the working or staple forming surface of anvil plate 90 while knife blade 36 cuts the tissue forming a knife cut line and needle 6 applies an adhesive into, on, or over the knife cut line, and, preferably also over one or more staple lines, especially where staple legs penetrate the tissue. In operation, prior to firing surgical stapling apparatus 10, actuation sled 28 is in the proximal-most position shown in FIG. 14. At such a time, knife blade 36 and the distal portion of conduit 8 are enclosed or protected in protective housing 25 formed adjacent the proximal end of disposable loading unit 20.

To fire the apparatus, firing knob 50 (see FIG. 2A) is moved in a distal direction. Accordingly, as illustrated in FIG. 15, actuation channel 44 drives actuation sled 28 distally into and through cartridge 22. During its distal translation, the angled leading surfaces of cam wedges 32 and 34 sequentially contact ejectors 26, urging them in a direction transverse to the direction of movement of actuation sled 28. As a result, ejectors 26 push staples 24 from their individual slots 22a, driving each staple into a respective staple forming cup 91 in anvil plate 90.

Sequential firing of the staples continues until actuation sled 28 is advanced to the distal end of cartridge 22, at which time, all of the staples once housed within cartridge 22 will have been ejected (see FIG. 16) and the knife cut line formed by knife blade 36 and preferably adjacent or all worked portions of the tissue have been supplied with wound closure material by wound closure material applicator assembly 2 including particularly needle 6. Thereafter, firing knob 50 is retracted to its original position, the cartridge and anvil sections are separated, and the spent disposable loading unit 20 is removed from retaining channel 14. Subsequently, a new, fully loaded disposable loading unit 20 can be positioned in retaining channel 14 such that slot 40 of actuation sled 28 engages flange 42 of actuation channel 44 to enable re-use of surgical stapling apparatus 10. Further, reservoir 4 may be replaced or refilled prior to re-use of surgical stapling apparatus 10.

Figure 17:
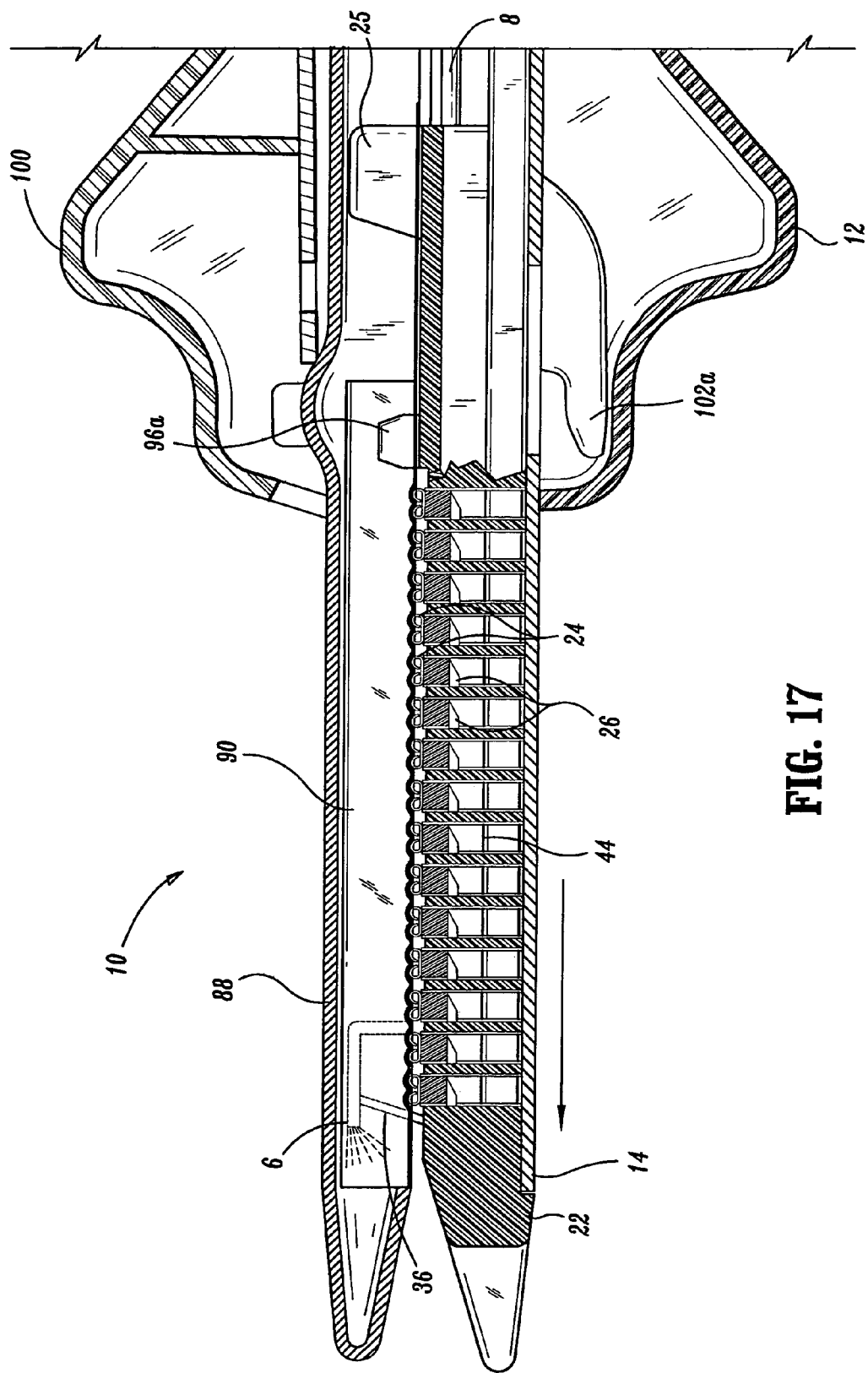
FIG. 17 is a side elevational view in cross-section of the surgical stapling apparatus of the subject application with the actuation sled advanced to the distal end of the cartridge at the conclusion of a staple firing procedure and a dispensing needle located near the knife blade.

With reference to FIG. 17 there is shown a side elevational view in cross-section of surgical stapling apparatus 10 with actuation sled 28 advanced to the distal end of cartridge 22 at the conclusion of a staple firing procedure and, in a variation of the embodiment, where dispensing needle 6 is shown located on the same side as and over knife blade 36 for dispensing adhesive on and/or in front of knife blade 36 during the staple firing procedure. Needle 6 in FIG. 17 can have orifices along its bottom surface to facilitate dispensing of wound closure material on, in front of, or near knife blade 36.

Figure 18A:
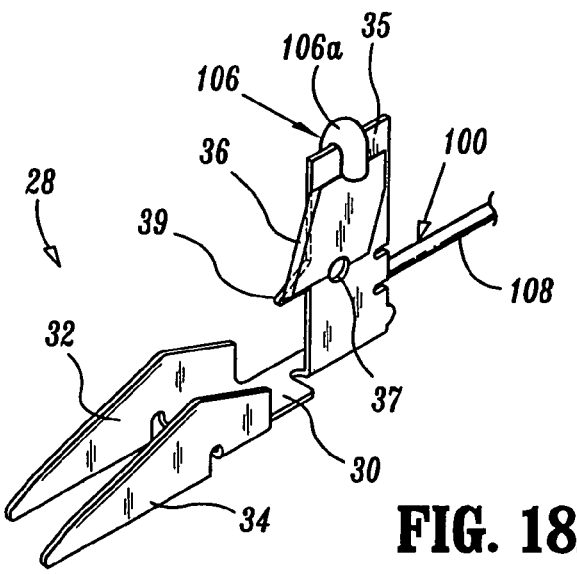
FIG. 18A is a perspective view of an actuation sled including a wound closure material applicator, in accordance with an alternative embodiment, operatively connected thereto.
Figure 18B:
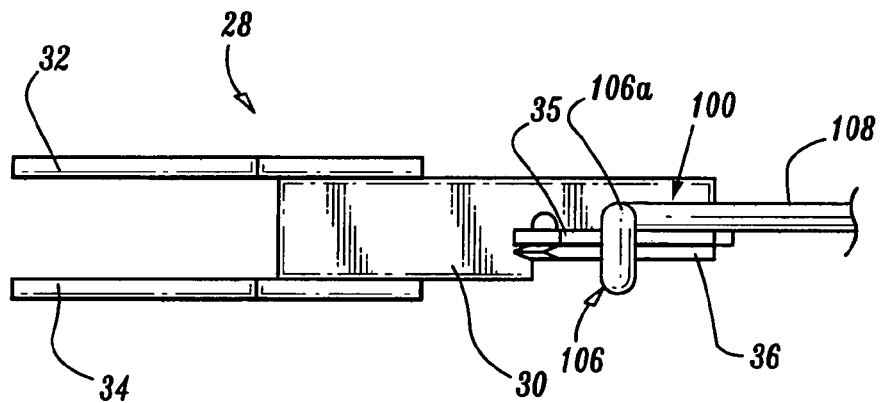
FIG. 18B is a top plan view of the actuation sled and applicator of FIG. 18A.
Figure 18C:
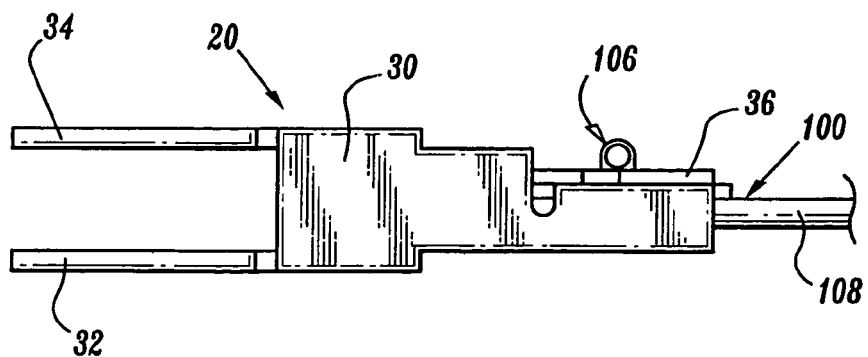
FIG. 18C is a bottom plan view of the actuation sled and applicator of FIG. 18A.

Turning now to FIGS. 18A-18C, an alternative embodiment of a portion of a wound closure material applicator assembly, generally designated as 100, is shown operatively connected to actuation sled 28. Wound closure material applicator assembly 100 includes a conduit 108 for transmitting wound closure material "W" from reservoir 4 (see FIG. 2A) and a needle 106, having a substantially inverted "J-shape", connected to a distal end of conduit 108. Needle 106 includes a hook portion 106a configured and dimensioned to hook over upstanding shank 35 such that a distal end of hook portion 106a includes an orifice that is oriented substantially downwardly. In an alternative embodiment, conduit 108 can itself be adapted, e.g. with an orifice, to perform the function of needle 106.

Figure 19A:
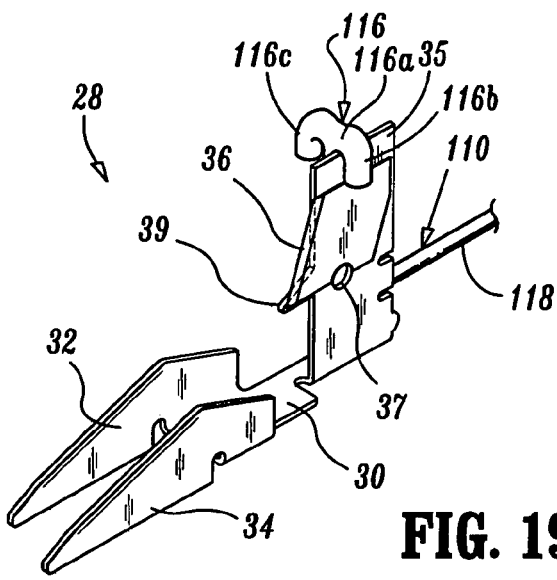
FIG. 19A is a perspective view of an actuation sled including a wound closure material applicator operatively connected thereto, in accordance with another embodiment.
Figure 19B:
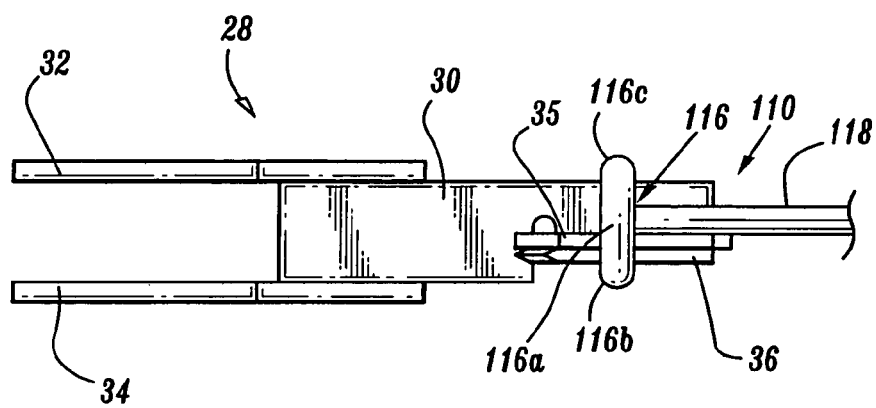
FIG. 19B is a top plan view of the actuation sled and applicator of FIG. 19A.
Figure 19C:
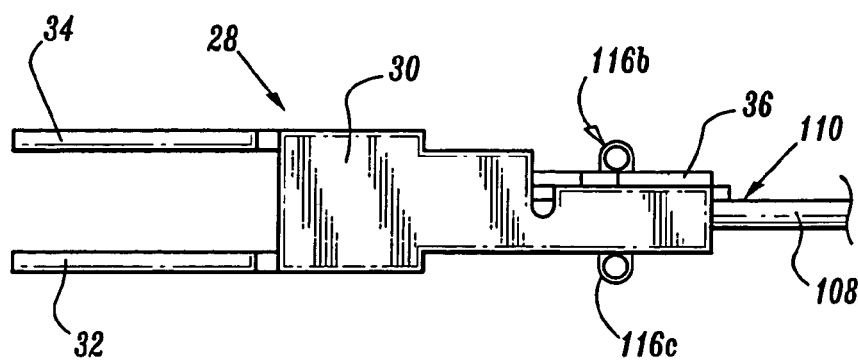
FIG. 19C is a bottom plan view of the actuation sled and applicator of FIG. 19A.

Turning now to FIGS. 19A-19C, a further alternative embodiment of a portion of a wound closure material applicator assembly, generally designated as 110, is shown operatively connected to actuation sled 28. Wound closure material applicator 110 includes a conduit 118 for transmitting wound closure material "W" from a source, e.g., reservoir 4 (see FIG. 2A), and a needle 116 connected to a distal end of conduit 118. Needle 116 includes a manifold head portion 116a having two substantially "U-shaped" tips 116b, 116c with orifices (not shown). Head portion 116a is preferably oriented such that tip 116b hooks over upstanding shank 35 of actuation sled 28 and tip 116c extends laterally from upstanding shank 35 in a direction substantially opposite to tip 116b. In this manner, wound closure material "W" can be dispensed on either side of upstanding shank 35.

Figure 20A:
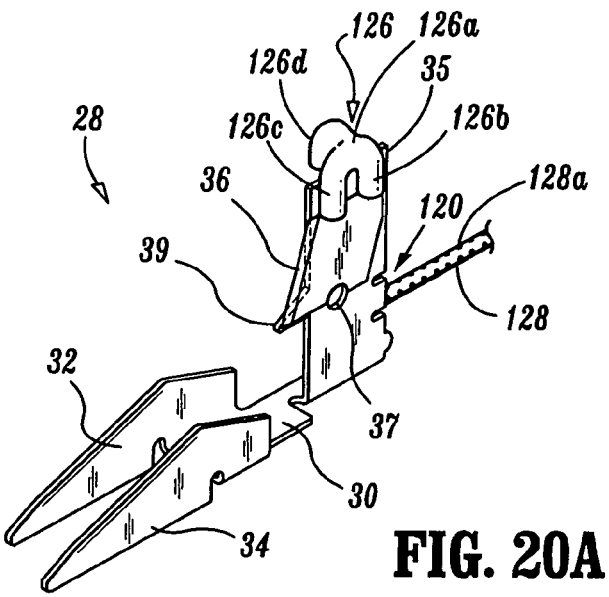
FIG. 20A is a perspective view of an actuation sled including a wound closure material applicator operatively connected thereto, according to yet another embodiment.
Figure 20B:
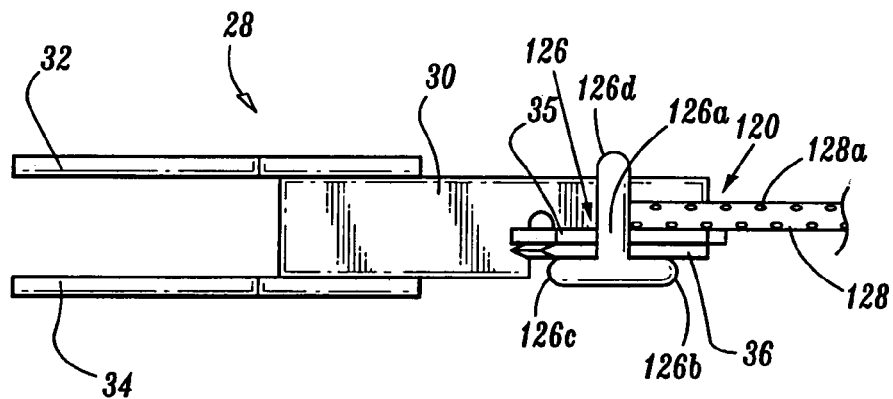
FIG. 20B is a top plan view of the actuation sled and applicator of FIG. 20A.
Figure 20C:
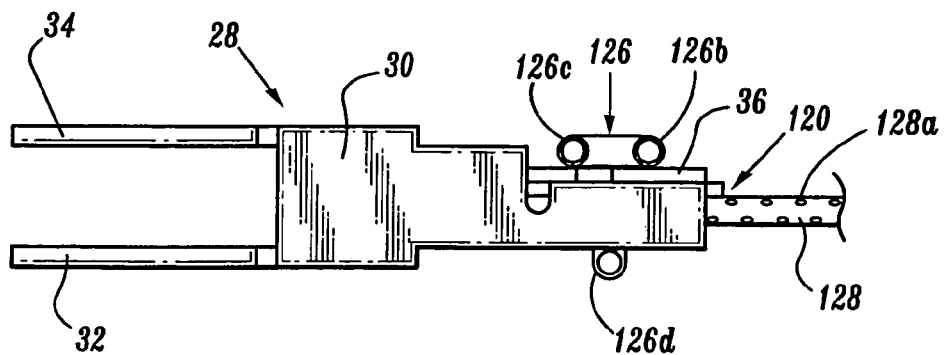
FIG. 20C is a bottom plan view of the actuation sled and applicator of FIG. 20A.

Turning now to FIGS. 20A-20C, a still further alternative embodiment of a portion of wound closure material applicator assembly, generally designated as 120, is shown operatively connected to actuation sled 28. Wound closure applicator 120 includes a conduit 128 for transmitting wound closure material "W" from reservoir 4 (see FIG. 2A) and a needle 126 fluidly connected to a distal end of conduit 128. Needle 126 includes a manifold head 126a having three "U-shaped" tips 126b, 126c, and 126d with orifices (not shown). Head portion 126a is preferably oriented such that tips 126*b*, 126*c* hook over upstanding shank 35 of actuation sled 28, and tip 126*d* extends laterally from upstanding shank 35 in a direction opposite tips 126*b*, 126*c*. In this manner, wound closure material "W" can be more widely dispersed on either side of upstanding shank 35. Alternatively, lip 126*c* can be extended to, or over, or beyond the distal edge of knife blade 36.

While wound closure material applicators having single (FIGS. 1-18C), double (FIGS. 19A-19C) and triple (FIGS. 20A-20C) distribution tips are shown and described, it is understood and within the scope of the present disclosure that any number of distribution tips and configurations can be provided for distributing wound closure material "W" along the staple line and/or the knife cut line.

While the distribution tips of FIGS. 18A-20C, have been shown as being oriented in a substantially downward direction, it is envisioned that the distribution tips can be oriented in a proximal, distal downward or upward direction or any combination thereof.

It is envisioned that each conduit 108, 118 and 128 shown herein can include at least one, preferably a plurality, of apertures 108*a*, 118*a*, and 128*a*, respectively, formed along a length thereof. Preferably, apertures 108*a*, 118*a*, and 128*a* are formed along the upper side and along the lateral sides thereof. In this manner, when wound closure material "W" is urged through conduits 108, 118, and 128, a quantity of wound closure material "W" is dispensed from apertures 108*a*, 118*a*, 128*a* along staple line and/or knife cut line.

Although FIGS. 18A-20C show a conduit disposed to the side of shank 35 of actuation sled 28, it is preferred that the conduit be disposed along the proximal or rear edge of the shank, sled, or like structure. The conduit and/or needle can be secured, connected to, or mounted permanently or removably on or to a sled, knife blade, or blade carrier structure in any suitable manner. Relative conduit and needle lengths and configurations can be modified to suit the application.

In any or all of the embodiments, or combinations thereof disclosed herein, at least a portion of the conduit can have openings or orifices along its side surface and/or its top surface and/or, especially, along its bottom surface such that wound closure material can be dispensed directly into and about the knife cut line, for example, as the conduit connected, for example, to actuation sled 28, with or without a needle, is moved axially along the cartridge and/or anvil.

It is to be understood that if openings are provided in a conduit, depending on the wound closure material and use, the openings may have to be temporarily previously sealed until it is desired to dispense the wound closure material through the conduit. This would apply, e.g. if the wound closure material were in the conduit or the needle, or applicator, such that its orifice(s) would need to be sealed. The seal can be burst by the fluid pressure applied by compression of reservoir 4 or other suitable, e.g. hydraulic or pressurized, system.

It is to be understood that the dispensing of wound closure material "W" can be as a fluid spray of any suitable volume, including a mist, applied temporarily, continuously, or continually. Particulate material, e.g. a fine powder is contemplated to be a fluid within the scope of this disclosure.

It is provided that a number of different wound closure materials "W" can be dispensed by wound closure material applicator assembly 2 or a combination of the number of different wound closure materials "W". The wound closure material dispensed by wound closure material applicator assembly 2 can, for example, be an astringent, such as a sulfate of aluminum, which causes small blood vessels to close and helps the blood to coagulate. It is provided that wound closure material "W" can be an astringent provided in the material commercially available under the trade designation No Nix Styptic Pencils from Requa™, Inc.

Although the subject apparatus has been described with respect to preferred embodiments, it will be readily apparent, to those having ordinary skill in the art to which it appertains, that changes and modifications may be made thereto without departing from the spirit or scope of the subject apparatus.

What is claimed is:

1. A surgical stapling apparatus for joining body tissue, comprising:
    a staple anvil positioned at a distal end of the stapling apparatus and having a knife track defined therein;
    a staple cartridge positioned adjacent the staple anvil, the staple cartridge and staple anvil being juxtaposable relative to each other, the staple cartridge including a plurality of surgical staples individually disposed within individual staple slots formed in rows in the staple cartridge, and having a knife slot formed between adjacent rows of staples;
    a driving member for firing the surgical staples from the individual staple slots and against the staple anvil;
    a staple actuator having at least one cam wedge for ejecting staples and a knife blade, the staple actuator being movable along the staple rows; and
    a wound closure material applicator assembly operatively associated with the stapling apparatus, the assembly including:
    a conduit for conveying a wound closure material from a location external of the staple anvil and the staple cartridge to the staple actuator, wherein the conduit extends proximally from the staple actuator; and
    a distribution tip in communication with the conduit and having an orifice, the conduit and the distribution tip being attached to the staple actuator so that the conduit and the distribution tip move along the staple rows with the staple actuator.

2. The surgical stapling apparatus as claimed in claim 1, wherein the distribution tip is arranged so that the orifice faces in a proximal direction.

3. The surgical stapling apparatus as claimed in claim 1, wherein the distribution tip is arranged so that the orifice faces the knife slot in the staple cartridge.

4. The surgical stapling apparatus as claimed in claim 1, wherein the distribution tip has more than one orifice.

5. The surgical stapling apparatus as claimed in claim 1, wherein more than one distribution tip is attached to the staple actuator.

6. The surgical stapling apparatus as claimed in claim 1, wherein the orifice is temporarily sealed and opens when the wound closure material reaches a predetermined fluid pressure.

7. The surgical stapling apparatus as claimed in claim 1, wherein the distribution tip moves longitudinally from a proximal end of the staple anvil and a distal end of the staple anvil.

8. A surgical stapling apparatus for joining body tissue, comprising:
    an anvil half-section having an anvil with a plurality of staple-forming recesses and a longitudinally extending knife track;
    a cartridge half-section juxtaposable with the anvil half-section and arranged for receiving a loading unit so that the loading unit is juxtaposed with the anvil, the loading unit including a plurality of surgical staples individually disposed within individual staple slots formed in longitudinally extending rows in the loading unit, and having a longitudinally extending knife slot formed between adjacent rows of staples;

a driving member for firing the surgical staples from the individual staple slots and against the staple anvil;

a staple actuator having at least one cam wedge for ejecting staples and a knife blade, the staple actuator being movable along the staple rows;

a conduit for conveying a wound closure material from a location external of the anvil half-section and the cartridge half-section to the staple actuator, wherein the conduit extends proximally from the staple actuator; and a distribution tip in communication with the conduit and having an orifice, the conduit and the distribution tip being attached to the staple actuator and arranged to distribute the wound closure material along the staple rows as the staple actuator, the conduit, and the distribution tip move along the staple rows.

9. The surgical stapling apparatus as claimed in claim 8, wherein the distribution tip is attached to the staple actuator.

10. The surgical stapling apparatus as claimed in claim 8, wherein the distribution tip is arranged so that the orifice faces in a proximal direction.

11. The surgical stapling apparatus as claimed in claim 8, wherein the distribution tip is arranged so that the orifice faces the knife slot in the staple cartridge.

12. The surgical stapling apparatus as claimed in claim 8, wherein the distribution tip has more than one orifice.

13. The surgical stapling apparatus as claimed in claim 8, wherein more than one distribution tip is attached to the staple actuator.

14. The surgical stapling apparatus as claimed in claim 8, wherein the orifice is temporarily sealed and opens when the wound closure material reaches a predetermined fluid pressure.

15. The surgical stapling apparatus as claimed in claim 8, wherein the driving member is longitudinally movable through the loading unit.

16. The surgical stapling apparatus as claimed in claim 15, further comprising a firing knob attached to the driving member.

17. The surgical stapling apparatus as claimed in claim 8, wherein the loading unit includes the staple actuator, the staple actuator being removably attached to the driving member, and the loading unit is replaceable.

18. The surgical stapling apparatus as claimed in claim 8, wherein the conduit and dispensing tip are replaceable.

19. The surgical stapling apparatus as claimed in claim 8, further comprising a reservoir for containing the wound closure material.

20. The surgical stapling apparatus as claimed in claim 19, wherein the reservoir is compressible.

21. The surgical stapling apparatus as claimed in claim 8, wherein the conduit transverses the length of the loading unit.

* * * * *